United States Patent
Wynn et al.

(10) Patent No.: US 10,602,931 B2
(45) Date of Patent: Mar. 31, 2020

(54) SYSTEM AND METHOD FOR NON-CONTACT ULTRASOUND WITH ENHANCED SAFETY

(71) Applicant: MASSACHUSETTS INSTITUTE OF TECHNOLOGY, Cambridge, MA (US)

(72) Inventors: Charles M. Wynn, Groton, MA (US); Robert W. Haupt, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 132 days.

(21) Appl. No.: 15/458,671

(22) Filed: Mar. 14, 2017

(65) Prior Publication Data

US 2017/0258332 A1     Sep. 14, 2017

Related U.S. Application Data

(60) Provisional application No. 62/307,758, filed on Mar. 14, 2016.

(51) Int. Cl.
 *A61B 5/00*   (2006.01)
 *A61B 8/08*   (2006.01)

(52) U.S. Cl.
 CPC ............ *A61B 5/0095* (2013.01); *A61B 5/742* (2013.01); *A61B 8/5207* (2013.01); *A61B 2576/026* (2013.01)

(58) Field of Classification Search
 None
 See application file for complete search history.

(56) References Cited

U.S. PATENT DOCUMENTS

| 4,554,836 A | 11/1985 | Rudd |
| 5,615,675 A | 4/1997 | O'Donnell |

(Continued)

FOREIGN PATENT DOCUMENTS

| DE | 102008049692 | 4/2010 |
| EP | 0996469 | 5/2000 |

(Continued)

OTHER PUBLICATIONS

Allen, et al., Generating Photoacoustic Signals Using High-Peak Power Pulsed Laser Diodes, Proc. SPIE, 2005, 5696:233-242.

(Continued)

*Primary Examiner* — Joel F Brutus
(74) *Attorney, Agent, or Firm* — Quarles & Brady LLP

(57) ABSTRACT

A system and method for noncontact ultrasound imagery capable of generating images in a manner that is safer for eyes and skin is provided. A photoacoustic excitation source may be employed to direct light signals with wavelengths of 1400-1600 nanometers into the patient to generate acoustic disturbances that induce propagating photoacoustic waves. The acoustic disturbances may be translated in defined directions to cause coherent summation of the propagating photoacoustic waves and, thereby, generate a resultant acoustic and/or elastic wave to probe structures within the patient. Vibrations created by the scatter of the resultant wave are detected at the surface of the patient and ultrasound images of the structures within the patient may be generated. Detection of the vibrations may be performed using a laser vibrometer. The excitation and detection systems may be used separately or in combination. Ultrasound images can be generated without physically contacting the patient.

24 Claims, 18 Drawing Sheets

(56) References Cited

U.S. PATENT DOCUMENTS

| | | | |
|---|---|---|---|
| 5,810,731 | A | 9/1998 | Sarvazyan |
| 5,840,023 | A | 11/1998 | Oraevsky |
| 6,292,682 | B1 | 9/2001 | Kruger |
| 8,203,911 | B2 | 6/2012 | Kremeyer |
| 8,260,403 | B2 | 9/2012 | Fukutani |
| 2008/0208044 | A1 | 8/2008 | Lecoq |
| 2008/0221647 | A1 | 9/2008 | Chamberland |
| 2009/0054763 | A1 | 2/2009 | Wang |
| 2009/0227997 | A1 | 9/2009 | Wang |
| 2010/0010346 | A1 | 1/2010 | Greenleaf |
| 2010/0245766 | A1 | 9/2010 | Zhang |
| 2011/0048135 | A1 | 3/2011 | Caron |
| 2011/0130660 | A1 | 6/2011 | Cloutier |
| 2011/0174078 | A1* | 7/2011 | Chinn ............... G01H 9/004 73/657 |
| 2012/0108968 | A1 | 5/2012 | Freiburger |
| 2012/0326055 | A1 | 12/2012 | Wilson |
| 2012/0330157 | A1 | 12/2012 | Mandella |
| 2013/0023752 | A1 | 1/2013 | Khuri-Yakub |
| 2013/0041247 | A1 | 2/2013 | Maswadi |
| 2014/0196544 | A1 | 7/2014 | Wanda |
| 2014/0243666 | A1 | 8/2014 | Moilanen |
| 2015/0148655 | A1* | 5/2015 | Haupt ............... A61B 8/0808 600/407 |
| 2015/0148675 | A1 | 5/2015 | Haupt |
| 2015/0335252 | A1 | 11/2015 | Hirota |
| 2015/0359478 | A1 | 12/2015 | Eyal et al. |
| 2016/0066786 | A1 | 3/2016 | Kontiola |

FOREIGN PATENT DOCUMENTS

| | | |
|---|---|---|
| WO | 2009103502 | 8/2009 |
| WO | 2013064740 | 5/2013 |

OTHER PUBLICATIONS

Berthelot, Yves H., and Ilene J. Busch-Vishniac. "Thermoacoustic radiation of sound by a moving laser source." The Journal of the Acoustical Society of America 81.2 (1987): 317-327.

Bozhkov, A. I., and Fedor V. Bunkin. "Generation of sound in a liquid as a result of absorption of modulated laser radiation." Soviet Journal of Quantum Electronics 5.8 (1975): 956.

Chance, B., et al. "Phase measurement of light absorption and scatter in human tissue." Review of scientific instruments 69.10 (1998): 3457-3481.

Haupt, et al., Standoff Acoustic Laser Technique to Locate Buried Land Mines, Lincoln Laboratory Journal, 2005, 15 (1):3-22.

International Search Report & Written Opinion for application PCT/US2017/022328, dated May 26, 2017, 12 pages.

Jacques, S. L. "Optical properties of biological tissues: a review." Physics in Medicine & Biology 58.11 (2013): R37.

Jiang, et al., Laser Vibrometry from a Moving Ground Vehicle, Applied Optics, 2011, 50(15):2263-2273.

Karppinen et al. "Phase-delayed laser diode array allows ultrasonic guided wave mode selection and tuning". Journal of Applied Physics, (Apr. 14, 2013 American Institute of Physics, US) vol. 113, nr. 14, pp. 144904-144904-5.

Li, et al., Photoacoustic Tomography and Sensing in Biomedicine, Phys. Med. Biol., 2009, 54(19):R59-R97.

Lyamshev, L. M., and L. V. Sedov. "Optical-Generation of Sound in a Liquid-Thermal Mechanism-Review." Soviet Physics Acoustics-USSR 27.1 (1981): 4-18.

Maslov, et al., Photoacoustic Imaging of Biological Tissue with Intensity-Modulated Continuous-Wave Laser, Journal of Biomedical Optics, 2008, 13(2):024006-1 thru 024006-5.

Moilanen, et al., Photo-Acoustic Phase-Delayed Excitation of Guided Waves in Coated Bone Phantoms, 2013 IEEE International Ultrasonics Symposium, 2013, pp. 2080-2083.

PCT International Search Report and Written Opinion, PCT/US2014/065001, Feb. 5, 2015.

Ripoll, et al., Quantitative Point Source Photoacoustic Inversion Formulas for Scattering and Absorbing Media, Phys. Rev. E, 2005, 71:031912 [Abstract Only].

Rousseau, et al., Non-Contact Photoacoustic Tomography and Ultrasonography for Tissue Imaging, Biomedical Optics Express, 2012, 3(1):16-25.

Schurig, et al., Signal Analysis of Transients in Pulsed Photoacoustic Spectroscopy, Review of Scientific Instruments, 1993, 64(2):363-373.

Shung. "Diagnostic Ultrasound: Imaging and Blood Flow Measurements." (2006).

Troy, T. L. et al. "Optical properties of human skin in the near infrared wavelength range of 1000 to 2200 nm." Journal of biomedical optics 6.2 (2001): 167-177.

Urban, et al. "A review of shearwave dispersion ultrasound vibrometry (SDUV) and its applications." Current medical imaging reviews 8.1 (2012): 27-36.

Wang, Tutorial on Photoacoustic Microscopy and Computed Tomography, IEEE Journal of Selected Topics in Quantum Electronics, 2008, 14(1):171-179.

Wynn, et al., Dynamic Photoacoustic Spectroscopy for Trace Gas Detection, Applied Physics Letters, 2012, 101:184103-1 thru 184103-4.

Xu, et al., Non-Contact Photoacoustic Tomography with a Laser Doppler Vibrometer, Proc. of SPIE, 2014, 8943:894332-1 thru 894332-7.

Xu, et al., Photoacoustic Imaging in Biomedicine, Review of Scientific Instruments, 2006, 77:041101-1 thru 041101-22.

Yin, et al., Fast Photoacoustic Imaging System Based on 320-Element Linear Transducer Array, Phys. Med. Biol., 2004, 49:1339-1346.

Gusev & Karabutov "Laser Optoacoustics" AIP, New York, 1993. (Split in 3 parts due to size).

Carter, D. R., et al. "Compact bone fatigue damage—I. Residual strength and stiffness." Journal of Biomechanics 10.5-6 (1977): 325-337.

\* cited by examiner

| Measurement Configuration | Excitation Source | Signal Sensor Receiver | Measured SNR (dB) |
|---|---|---|---|
| Full sample contact | 1 MHz longitudinal piezoelectric transducer | 1 MHz longitudinal piezoelectric transducer | 39 |
| Contact excitation/ optical measurement | 1 MHz longitudinal piezoelectric transducer | 2.5 MHz Polytec LDV (reflexite bead surface treatment) | 32 |
| Total optical, no contact | 355 nm; 10 nS optical pulse | 2.5 MHz Polytec LDV (reflexite bead surface treatment) | 37 |
| Contact excitation/ optical measurement | 1 MHz longitudinal piezoelectric transducer | 2 MHz MIT LL Custom LDV (no sample surface treatment) | 22 |
| Total optical, no contact | 355 nm; 10 nS optical pulse | 2 MHz MIT LL Custom LDV (no sample surface treatment) | 19 |

FIG. 8

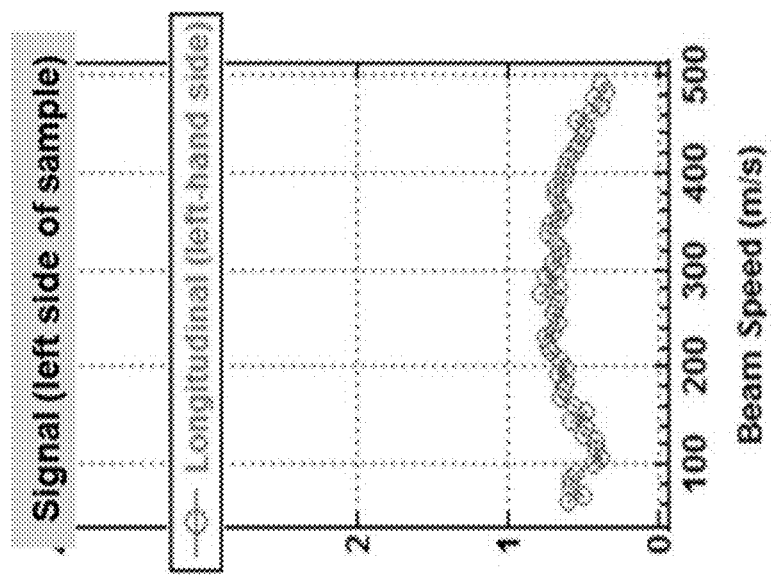
FIG. 20
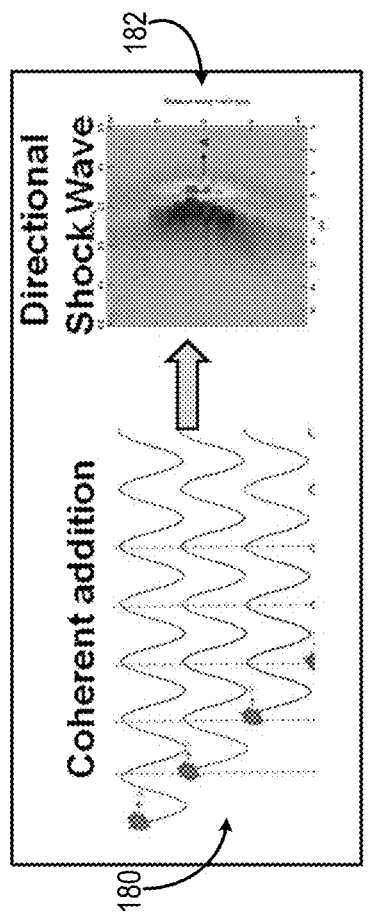
FIG. 18
FIG. 19

SYSTEM AND METHOD FOR NON-CONTACT ULTRASOUND WITH ENHANCED SAFETY

CROSS-REFERENCE TO RELATED APPLICATIONS

This application is based on, claims priority to, and incorporates herein by reference in its entirety U.S. Provisional Application Ser. No. 62/307,758, filed Mar. 14, 2016, and entitled, "Eye and Skin Safe Means of Creating Photoacoustic Energy within the Human Body."

STATEMENT REGARDING FEDERALLY SPONSORED RESEARCH

This invention was made with government support under FA8721-05-C-0002 awarded by the U.S. Air Force. The government has certain rights in the invention.

BACKGROUND OF THE INVENTION

The present invention relates to systems and methods for generating ultrasound images, and more particularly to systems and methods for generating ultrasound images without system contact to the patient, which may be achieved, for example, using photoacoustic energy and/or laser vibrometry, in a manner that is safer for the eyes and skin.

Acoustic energy is used in numerous applications to characterize discontinuities, defects, and other mechanical properties within various types of materials. Acoustically-based techniques rely on differences in mechanical properties between a feature of interest and its local surroundings. These differences result in different vibrational responses to sonic excitation, which may be detected and the feature thereby localized and/or characterized.

An important advantage of acoustic techniques is the ability to detect discontinuities corresponding to (or indicating the presence of) flaws or hidden items that may not be detectable using visual or other techniques. Such discontinuities may represent latent defects that can compromise the mechanical integrity of load-bearing structures. Coupling a sufficient amount of acoustic energy into the medium of interest is critical, and in many cases it is the factor most limiting the efficacy of the technique. The large impedance mismatch between the ambient air and most solids or liquids makes the transfer of acoustic energy into the medium a generally inefficient process. Loudspeakers are omnidirectional thus suffering significant losses at large ranges. Parametric acoustic array (PAA) sources can provide directionality, but are limited to ranges on the order of tens of meters. An efficient means of coupling acoustic energy into media could have wide ranging benefits.

Ultrasonic imaging of the internal details of the human body can provide advantages relative to other techniques such as X rays (soft tissue contrast) and MRIs (faster and less cumbersome data acquisition). Typically, ultrasonic imagery is obtained in a "contact" manner in which an ultrasonic transducer (which both sends and receives the acoustic signals) is placed directly on (i.e., in contact with) the area of interest. Because of the very large acoustic impedance mismatch between air and the human body (acoustic coupling efficiency is only about $10^{-3}$), a coupling gel is generally used at the interface between transducer and tissue to increase coupling efficiency into the body. A range of contact ultrasound techniques exist. In general, an acoustic pulse is emitted into to the body. Echoes from structures are reflected back to the transducer, with the time of arrival giving information about the range to the structure. In a simple but fairly standard incarnation, the acoustic source is omnidirectional, thus only range information is obtained. A two-dimensional image is formed by using a line of transducers, which yield information in the cross range direction.

In certain circumstances, noncontact operation is highly desirable. If used in conjunction with a remote array source, it has the potential to mitigate the problems mentioned above related to 2D arrays. Additionally, there exist surgical situations in which sterility is an issue, situations in which contact is unpleasant or painful (such as imaging the eye), or emergency situations in which the patient is in transit and/or being stabilized and may not be easily imaged via a contact system. In certain triage situations it may be desirable to image multiple patients in as rapid a manner as possible, and a noncontact system may be able to provide this capability. Additional applications include, real-time surgical feedback imaging, traumatic brain injury (TBI) detection, bone health monitoring, and others. For example, real-time surgical guidance and feedback would greatly improve from an imaging technique that can directly access exposed skin or traumatized tissue without contact, especially in very delicate procedures such as spinal and neck surgery. Using a laser system eliminates couple gels (used in conventional ultrasound) applied on skin that can contaminate open body tissues. In addition, a laser system can provide fine spatial and temporal resolution to yield high quality images while reducing distortion observed with contact sensing deformation. Other benefits of such a system minimize patient discomfort over injured areas and setup times to acquire images, and are unlikely to interfere with other methods such as MRI, CT scan, fluoroscope, etc. A portable, lightweight non-contact ultrasonic vibration imaging device can provide very significant advantages over traditional ultrasonic contact devices. Ideally, a low power handheld laser imaging system can be used not only in a hospital setting, but would provide tremendous benefits in field operations. However, existing photoacoustic systems are limited in applicability due to safety concerns, as the lasers used in such systems could be harmful to patients, causing damage to, for example, the skin and eyes of patients.

Thus, there is a need for systems and methods capable of providing an efficient means for coupling acoustic energy into media in a noncontact manner to generate ultrasound images in a manner that does not pose an unacceptable risk of damage to patients, and in particular, to the eyes and skin of patients.

SUMMARY OF THE INVENTION

The present invention overcomes the aforementioned drawbacks by providing a non-contact ultrasonic imaging device. The present invention may use a laser imaging system that provides an acoustic amplitude that is significantly larger than that induced via standard photoacoustic means. Coherent summation of the propagating acoustic and/or elastic waves is achieved by scanning the laser source along the surface of the body at the speed of sound. The present invention may also use an array of vibrometer detectors to determine the mechanical modulus of the surface of a patient's skin.

The present invention provides a method for generating ultrasound images of a patient. The steps of the method include directing a photoacoustic excitation source into a scanning mirror to transmit acoustic disturbances into the patient to induce propagating photoacoustic waves. The plurality of acoustic and/or elastic disturbances are translated along the patient in a defined direction to cause a coherent summation of the propagating photoacoustic waves. The coherent summation generates a resultant wave that propagates along the defined direction to probe structures within the patient. Vibrations are detected at a surface of the patient created by backscatter of the resultant wave from the structures within the patient. Ultrasound images of the structures within the patient are then generated using the vibrations previously detected at the surface of the patient.

The present invention also provides a system for generating ultrasound images of a patient. The system includes a photoacoustic excitation source directed into a scanning mirror to transmit acoustic disturbances into the patient to induce propagating photoacoustic waves. The system also includes a sensor configured to detect vibrations at a surface of the patient created by backscatter of a resultant wave. A data acquisition system is configured to receive the resultant wave. The system also includes a processor that has access to the data acquisition system to translate the acoustic disturbances along the patient in a defined direction to cause a coherent summation of the propagating photoacoustic waves. The coherent summation results in the resultant wave that propagates along the defined direction to probe structures within the patient. The processor then measures the vibrations at the surface of the patient created by backscatter of the resultant wave from the structures within the patient. The processor then generates ultrasound images of the structures within the patient using the vibrations detected at the surface of the patient.

The present invention also provides a method for generating ultrasound images of a patient. The steps of the method include directing a laser source configured to produce a laser beam toward the patient to induce propagating photoacoustic waves. The laser beam is then translated along the patient in a defined direction to cause a coherent summation of the propagating photoacoustic waves and, thereby, a resultant wave that propagates along the defined direction to probe structures within the patient. Vibrations are detected, using a laser vibrometer sensing array, at a surface of the patient created by backscatter of the resultant wave from the structures within the patient. Ultrasound images of the structures within the patient are then generated using the vibrations detected at the surface of the patient.

The present invention also provides a system for generating ultrasound images of a patient. The system includes a laser source configured to produce a laser beam directed towards the patient to induce propagating photoacoustic waves. The system also includes a laser vibrometer sensing array configured to detect vibrations at a surface of the patient created by backscatter of a resultant wave. A data acquisition system configured to receive the resultant wave. The system also includes a processor that has access to the data acquisition system to translating the laser beam along the patient in a defined direction to cause a coherent summation of the propagating photoacoustic waves and, thereby, the resultant wave that propagates along the defined direction to probe structures within the patient. The processor may also be configured to measure the vibrations, using the laser vibrometer sensing array, at the surface of the patient created by backscatter of the resultant wave from the structures within the patient. The processor may then generate ultrasound images of the structures within the patient using the vibrations detected at the surface of the patient.

To generate images in a manner that enhances safety for the eyes and skin, a photoacoustic excitation source may be employed that directs light signals with wavelengths of 1400 nanometers to 1600 nanometers into a patient for generating acoustic disturbances that induce propagating photoacoustic waves. The acoustic disturbances may be translated along the patient in a defined direction to cause coherent summation of the propagating photoacoustic waves and, thereby, generate a resultant acoustic and/or elastic wave to probe structures within the patient. Vibrations created by the scatter of the resultant wave are detected at the surface of the patient and ultrasound images of the structures within the patient are generated. Detection of the vibrations may be performed using a laser vibrometer. The excitation and detection systems may be used separately or in combination. Ultrasound images can be generated without physically contacting the patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 8 is a table showing signal-to-noise-ratio (SNR) comparisons for contact and optical ultrasonic measurement systems.

FIG. 18 is a diagram showing coherent addition of photoacoustic waves resulting in directional acoustic waves with a relatively strong signal amplitude.

FIG. 19 is a graph showing a continuous wave laser swept at various beam speeds at a right side of a sample.

FIG. 20 is a graph showing a continuous wave laser swept at various beam speeds at a left side of a sample.

DETAILED DESCRIPTION OF THE INVENTION

As will be described, the present invention includes a variety of systems and methods that may be used alone or in combination. For example, one component described hereafter includes a system for using photoacoustic excitation phenomena to generate propagating elastic waves into the body that can then reflect, refract, scatter, and absorb off interior structures. In this regard, a non-contact photoacoustic excitation source is provided that can steer the ultrasonic elastic wave beam as desired into the body. These elastic waves then propagate back to the skin surface, where they are measured and used to facilitate analysis of the body. Another component described hereafter includes a non-contact laser vibrometer or a non-contact digital focal plane array (DFPA), which can be used to provide a flood illumination of the skin surface. In this regard, the vibrometer or DFPA system can be used to measure the above-referenced elastic waves or can be used separately for other purposes. In the case of measuring returns of the above-described elastic wave, the returns can be processed and constructed to form a reflection image of the body interior based on elastic wave impedance contrast. The vibrometry and/or DFPA sensing devices can provide motion compensation capabilities for a static or moving detector platform or a static or moving subject that enables a resolved image. Without these capabilities, the return signal is not resolvable for moving systems.

The photoacoustic effect may be used as a means to couple acoustic energy into a human subject. The photoacoustic effect is a well-known process by which optical energy, typically from a laser, is absorbed by a medium. This transfer of energy results in a thermal expansion of the medium, which will result in a propagating acoustic and/or elastic wave. Many of the properties of the resulting acoustic and/or elastic wave can be controlled by the source laser within the material limitations of the source medium. Using a laser system eliminates coupling gels that are conventionally used in ultrasound imaging and applied to the patient's skin that can contaminate open body tissues. In addition, a laser system can provide fine spatial and temporal resolution to yield higher quality images while reducing distortion observed with contact sensing deformation. Biomedical photoacoustic systems can use laser wavelengths in the visible to near infrared (i.e., 400-1100 nm), which have absorption depths of approximately 0.1-10 cm. However, the actual penetration depth is usually less than the absorption depth due to significant optical scattering. In addition, existing photoacoustic systems utilize a single source of optical illumination with a fairly weak resultant acoustic response, making it difficult to probe structures within the patient.

Figure 1:
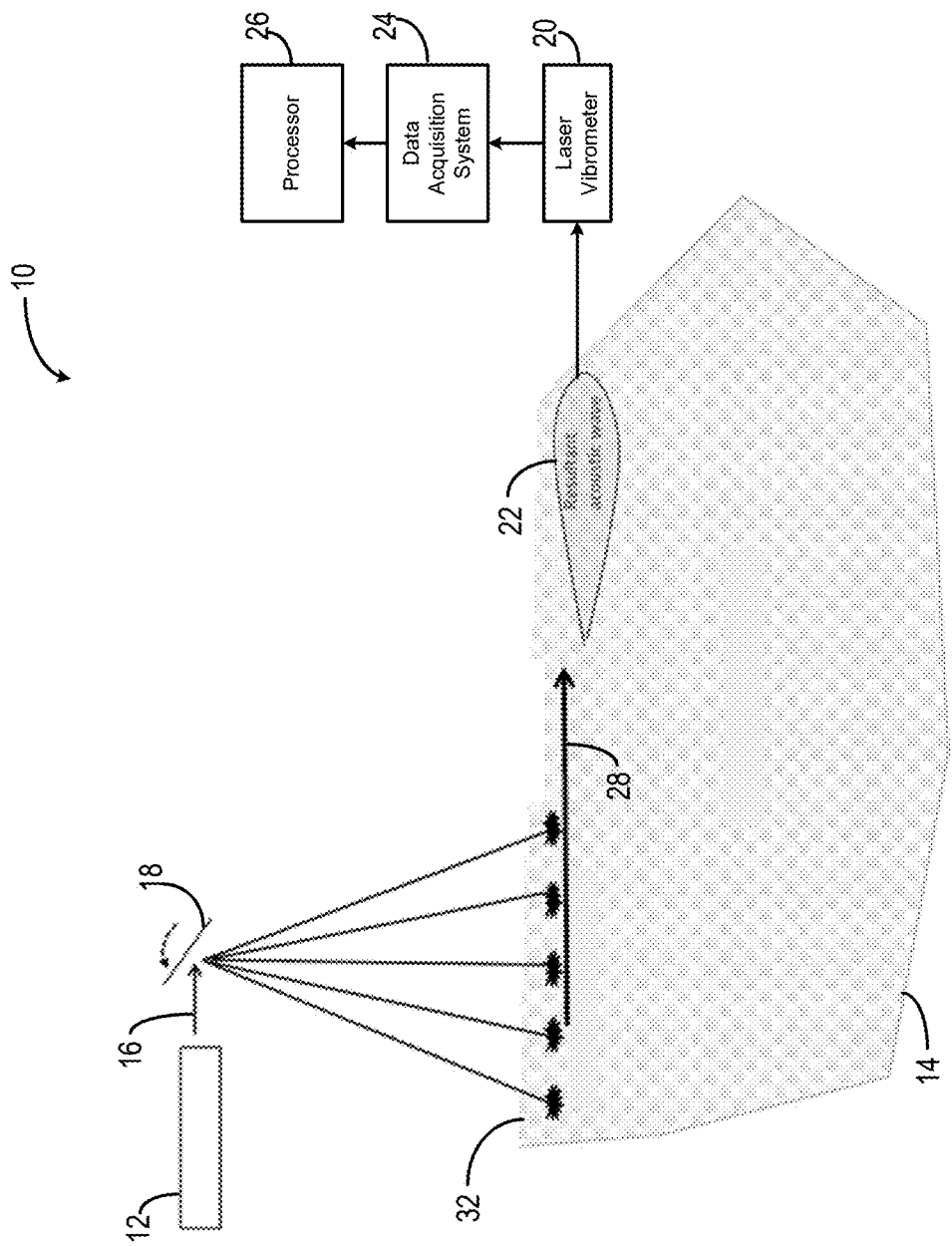
FIG. 1 is a schematic diagram showing a system configured to implement the present invention for generating ultrasound images.
Figure 2:
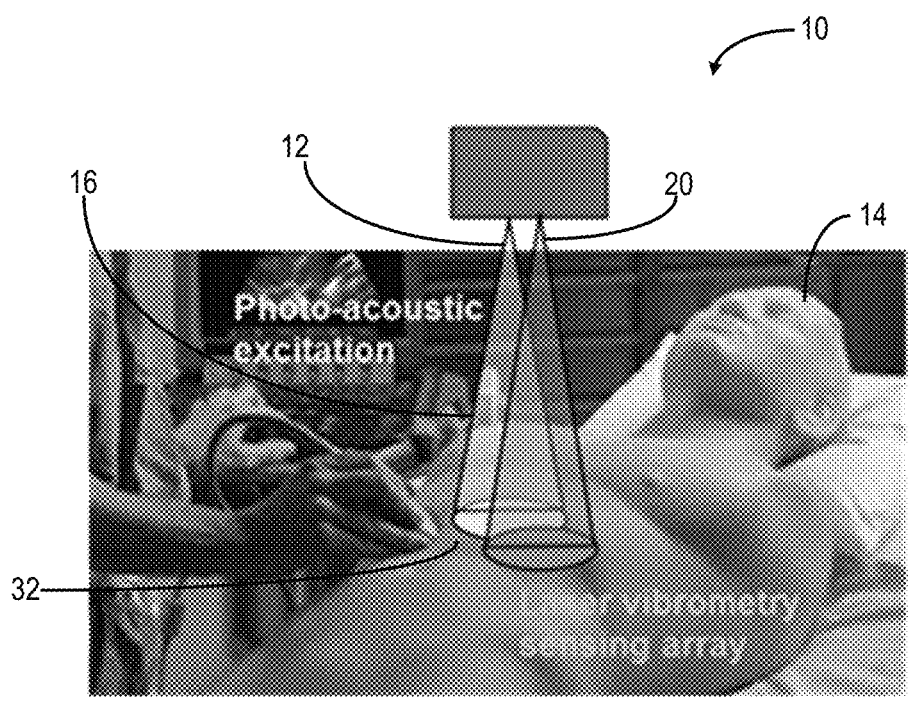
FIG. 2 is an image showing an excitation source and sensing array configured to be implemented into the system of FIG. 1.

Referring now to FIGS. 1 and 2, a system 10 is shown that provides a means to propagate acoustic energy in a single direction so that the acoustic amplitude can be larger than that induced via standard photoacoustic means. The system 10 may include a photoacoustic excitation source 12 configured to transmit acoustic disturbances into a patient 14 to induce propagating photoacoustic waves. The photoacoustic excitation source 12 may be, for example, a directed source of radio frequency energy or microwave energy. Alternatively, the photoacoustic source 12 may be a handheld device, such as a laser source configured to produce a modulating frequency between about 0 Hz to 10 MHz. Likewise, the photoacoustic source 12 may be a continuous wave (CW) laser. The photoacoustic source 12 may be arranged remotely from the patient 14 and produce a laser beam 16 directed at a scanning mirror 18 to transmit the acoustic disturbances into the patient 14. A sensor 20, for example, a laser vibrometer sensing array or an ultrasonic transducer receiver, may be positioned remotely from the patient 14 to detect vibrations created by backscatter of a resultant wave 22, as shown in FIG. 1. The resultant wave 22 may be generated by a coherent summation of the propagating photoacoustic waves. A data acquisition system 24, as shown in FIG. 1, may be coupled to the sensor 20 to receive the resultant wave 22 and a processor 26 may be coupled to the data acquisition system 24.

As shown in FIG. 1, the processor 26 may be configured to translate the acoustic disturbances along the patient 14 in a defined direction 28, as indicated by the arrow in FIG. 1, by rotating either the scanning mirror 18 or translating the photoacoustic excitation source 12 such that the laser spot incident upon the patient moves at the speed of sound, for example. This translation results in the coherent summation of the propagating photoacoustic waves to produce the resultant wave 22. The beam 16 is moved along the defined direction 28. For example, the mirror 18 may be moved to thereby move the beam 16 along the defined direction 28. Also, though more cumbersome, the source 12 can be moved. The processor 26 may also be configured to measure the vibrations at a surface 32 of the patient 14. The vibrations are created by the backscatter of the resultant wave 22 from probing the structures within the patient 14. The processor 26 may then generate ultrasound images of the structures within the patient using the vibrations detected by the sensor 20.

Figure 3A:
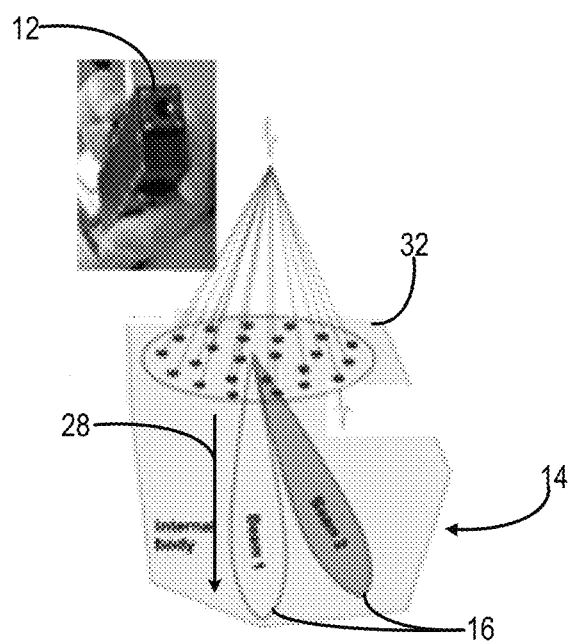
FIG. 3A is a diagram showing an excitation source to be implemented into the system of FIG. 1.

Referring now to FIG. 3A, the photoacoustic excitation source 12 is shown as a handheld laser source. The handheld laser source may be used to generate elastic wave propagation into the body. The non-contact laser excitation source generates acoustic/ultrasonic waves that travel into the patient 14 and return back to the skin surface 32. The laser source may be timed/phased to transmit the laser beam 16 that propagates in the defined direction 28 in order to scan the structures of the patient 14 at locations deeper than the optical penetration depth. The laser source may be, for example, a low-powered laser system that can generate acoustic/ultrasonic bandwidths and power levels that propagate into the patient 14, return to the skin surface 32, and that can be readily used to form ultrasound images. Thus, the laser source provides a controlled directional source of acoustic energy to probe and image specific structures of the patient 14. Advantageously, the acoustic and/or elastic waves have a directionality that eases the ability to generate three-dimensional ultrasound images.

Figure 3B:
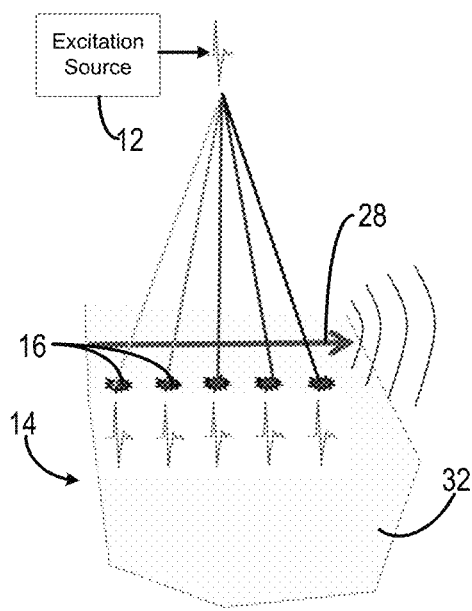
FIG. 3B is a diagram showing another excitation source to be implemented into the system of FIG. 1.

Alternatively, as shown in FIG. 3B the photoacoustic excitation source 12 may be translated along the patient 14, or example, at the speed of sound, in a defined direction to cause a coherent summation of the propagating photoacoustic waves. The coherent summation of the propagating photoacoustic waves results in generation of a directional resultant wave. Coherent summation of the propagating photoacoustic waves has the advantage that the wave amplitudes, rather than intensities, add, leading to a stronger overall resultant wave. The resultant wave may propagate along the defined direction to probe structures of the patient's 14 body.

Referring back to FIGS. 1 and 2, once the photoacoustic excitation source 12 is used to induce the propagating photoacoustic waves into the patient 14, the waves scatter, reflect, and refract in relation to the tissue mechanical property contrasts. As the propagating photoacoustic waves are backscattered towards the surface 32, vibrations are induced at the surface 32. The vibrations may be detected and measured remotely without contacting the patient 14 using the sensor 20 (i.e., the laser vibrometer sensing arrays). The sensor 20 operates as interferometer, for example, that emits a beam of light configured to be safely delivered to an eye or skin of the patient 14. The sensor 20 may be for example, a Coherent Multipixel Imaging system or a Digital Focal Plane Array (DFPA). The sensor 20 receives the spatially distributed acoustic/ultrasonic return from the body interior. These signals are then processed by the processor 26, as shown in FIG. 1, to form structural 2D and 3D ultrasound images of the interior structures of the patient 14.

The sensor 20 can measure vibrations over a frequency band from 1 Hz ranging to 40 MHz, for example. The sensor 20 may include firmware, for example, that utilizes Doppler tracking to compensate for movement of the patient 14. Further, the sensor 20 may provide motion-compensation capabilities that enable measurement of transmitted elastic waves in the body from a moving reference such as the handheld laser source 12, as shown in FIG. 3A. Thus, elastic wave excitation and measurement can be performed from as little as a few inches away from the patient 14 to as much as 30 meters, for example, from the patient 14.

In one non-limiting example, the photoacoustic excitation source 12 may be an optical source configured to generate acoustic and elastic waves in the body of the patient 14 from a standoff-noncontact position. More specifically, the optical source may generate a short optical frequency pulse to initiate and generate ultrasonic waves into tissue of the patient 14, which are driven by the primary mechanism of photoacoustic phenomena. Photoacoustic phenomena first develop from the photons that impinge on a target surface emitted from an optical source and the conversion of the photons into heat by the absorbing material, such as a fluid or biological tissue complex. This process may be a non-linear thermal shock loading that enables low Q tissue to deform rapidly and thus, generates ultrasonic acoustic and elastic waves.

In a first stage of the photoacoustic process, photons are absorbed by particles comprising a tissue volume, where the absorption coefficient $\mu_a$ is described below by equation (1):

$$\mu_a = \rho \sigma_a \text{ where, } \sigma_a = -4\frac{2\pi a}{\lambda}\pi a^2 \text{Im}\left\{\frac{n_1 - n_0}{n_1 + 2n_0}\right\} \quad (1)$$

where $\rho$ and $\sigma_a$ are the particle density and cross-sectional area, respectively, and a is the particle radius, where a << the optical wavelength, and $n_1$ and $n_0$ are the refraction indicies, respectively, of the absorbing material and an infinite homogeneous non-absorbing medium.

For an optical pulse incident on tissue particles, the total absorbed energy, $E_a$ may be described according to equation (2) below:

$$E_a(r, t) = \mu_a \int_{4\pi} I(r, t, \hat{s}) d\Omega = \mu_a U^{inc}(r, t) \quad (2)$$

Where I is the specific intensity absorbed by the tissue particles at a position r from light incident in a direction $\hat{s}$. $U^{inc}$ may be the average incident intensity with units of J/cm$^2$. The average incident intensity may be of particular concern when developing an optical laser ultrasound where the intensity is within eye and skin safe limits for the duration of optical radiation. In one example, 1-20 mJ/cm$^2$ is likely to meet safety requirements in the operational system 10.

The governing relationship establishing tissue deformation and thus, acoustic or elastic wave generation evolves from the tissue temperature increase caused by the absorbed energy as shown in equation (3) below:

$$\rho_m C \frac{\partial T(r, t)}{\partial t} - \kappa \nabla^2 T(r, t) = E_a(r, t) \quad (3)$$

Where $\rho_m$, C, $\kappa$, T are the tissue mass density, specific heat, thermal conductivity, and temperature, respectively. The first term shown in equation (3) describes the temperature increase due to optical absorption and diffusion. The optical diffusion may be several orders of magnitude larger than that of the thermal diffusion, thus, the second term shown in equation (3) may be negligible and the temperature increase due to the optical pulse radiation can be described by equation (4) below:

$$\frac{\partial T(r, t)}{\partial t} \approx \frac{1}{\rho_m C} \mu_a U^{inc}(r, t) \quad (4)$$

In addition, equation (4) may imply that thermal diffusion can be neglected since the optical pulse duration is considerably smaller than the time scale of thermal diffusion.

The effect of optical propagation into a scattering media, such as complex biological tissues, may be another component to understanding the process of photoacoustic phenomenology. Typically, the materials comprising tissue mass are considerably heterogeneous, where blood hemoglobin, for example, is highly absorptive to light while other tissue cells are simultaneously, highly reflective. Light and optical frequency waves may propagate in tissue and can be described by a diffusion approximation as shown in equation (5) below. The diffusion of the optical average intensity, U due to an incident energy density, $S_0$ is as follows:

$$D\nabla^2 U(r,t) - \frac{1}{c}\frac{\partial U(r,t)}{\partial t} - \overline{\mu_a}(r)U(r,t) = -S_0(r,t) \tag{5}$$

In equation (5) above, D may be the optical diffusion coefficient and c may be the average speed of light in the tissue. The average intensity experienced in a homogeneous scattering tissue column can then be related to the average incident energy as a function of frequency according to equation (6) below:

$$\tilde{U}(r,\omega) = \tilde{U}^{inc}(r_s,r) + \frac{1}{4\pi}\int_V \tilde{U}^{inc}(r_s,r')\Delta\mu_a(r') \times g(\gamma_0|r-r'|)dr' \tag{6}$$

In equation (6) above, g may be a 3D Green's function, for example, and $\gamma_0$ may be the frequency-dependent wave number for the optical diffuse photon density wave. The average incident energy can be derived showing the relationship between the incident energy density in the time domain according to equation (7) below:

$$U^{inc}(r_s,r,t) = \frac{S_0}{(4\pi Dct)^{3/2}}\exp\left[\frac{|r_s-r|}{4Dct} - \mu_a|r_s-r|\right] \tag{7}$$

The acoustic or elastic wave that can be measured by the sensor 20, such as an optical receiver including a laser Doppler vibrometer or conventional contact transducer, is another component to describing photoacoustic conversion of light to pressure and resultant acoustic wave propagation. For simplicity, an inviscid fluid may be used to demonstrate the generation and propagation of the longitudinal or compressional wave from incident light, as shown in the linear force equation (8) below:

$$\rho_m \frac{\partial^2 u(r,t)}{\partial t^2} = -\nabla p(r,t) \tag{8}$$

where u may be the acoustic displacement and p may be the acoustic pressure. The tissue media may then deform from expansion according to equation (9) below:

$$\nabla \cdot u(r,t) = -\frac{p(r,t)}{\rho_m v_s^2} + \beta T(r,t) \tag{9}$$

where $\beta$ is the volume expansion coefficient and $v_s$ is the acoustic speed in the tissue.

$$\nabla^2 p(r,t) - \frac{1}{v_s^2}\frac{\partial^2 p(r,t)}{\partial t^2} = \rho_m \beta \frac{\partial^2 T(r,t)}{\partial t^2} \tag{10}$$

Combing equations (9) and (10) above, the relationship between the heat source and the resultant pressure is shown below in equation (11) in terms of the optical average intensity and optical absorption coefficient:

$$\nabla^2 p(r,t) - \frac{1}{v_s^2}\frac{\partial^2 p(r,t)}{\partial t^2} = \frac{\beta}{c}[\mu_a + \Delta\mu_a(r)]\frac{\partial U(r,t)}{\partial t} \tag{11}$$

The pressure distribution along the tissue column resolves to equation (12):

$$p(r,t) = p_0(r,t) + \frac{\beta}{4\pi C}\int_V \frac{dr'}{|r-r'|}\Delta\mu_a(r') \times \left|\frac{\partial U^{inc}(r',t')}{\partial t'}\right|_{t'=t-\frac{|r-r'|}{v_s}} \tag{12}$$

Where $$p_0(r,t) = \frac{\beta\mu_a}{4\pi C}\int_V \frac{dr'}{|r-r'|}\left|\frac{\partial U^{inc}(r',t')}{\partial t'}\right|_{t'=t-|r-r'|/v_s}$$

In equation (12) above, $p_0(r,t)$ may be the incident pressure at the onset of the tissue column.

Once the photoacoustic excitation source 12 described above transmits acoustic disturbances into the patient 14, the sensor 20, such as a noncontact laser vibrometer sensing array, may measure the ultrasonic returns. The ultrasonic returns may be stimulated by the optical excitation sources that arrive from internal boundaries composing structures and material property distributions inside the patient 14, for example. In one non-limiting example, the sensor 20 is an optical heterodyne ladar design utilized for the vibrometer sensing system.

In conventional heterodyne detection, a signal of interest at a known frequency is non-linearly mixed with a reference "local oscillator" (LO) that is set at a close-by frequency. The desired outcome may be the difference frequency, which carries the signal information (i.e., amplitude, phase, and frequency modulation) of the original higher frequency signal, but is oscillating at a lower more easily processed carrier frequency. Electrical field oscillations in the optical frequency range cannot be directly measured since the relatively high optical frequencies have faster oscillating fields than electronics can respond. Instead, optical photons are detected by energy or equivalently by photon counting, which are proportional to the square of the electric field and thereby form a non-linear event. Thus, when the LO and the signal beams impinge together on a target surface, such as the surface 32 of the patient 14, the LO and signal beams "mix" and produce heterodyne beat frequencies.

The performance of a laser vibrometer, for example, and the process of ultrasonic wave measurement may be determined by the noise floor of the laser vibrometer. The noise floor may include, but is not limited to, 1) shot noise that dominates the noise floor at ultrasonic frequencies, 2) speckle noise that contributes noise in the audible acoustic band, and 3) platform and subject target vibration caused by motion by a variety of potential sources other than the intended system optical excitation source.

Shot noise may arise from statistical fluctuations in measurements. The detected electrical current for a heterodyne ladar may be described according to equation (13) below:

$$i(t) = i_{LO} + i_s(t) + 2\sqrt{\eta_h i_{LO} i_s(t)} \cos[\omega_{IF} t + \theta(t)] \quad (13)$$

where $i_{LO}$ and $i_s(t)$ are the currents from the local oscillator and signal, $\eta_h$ is the heterodyne mixing efficiency (0 to 1), $\omega_{IF}$ is the intermediate frequency (carrier signal is mixed with the local oscillator to produce a difference or beat frequency to improve signal gain), and $\theta(t)$ is the phase shift. $\omega_{IF}$ is equal to the acousto-optic modulator frequency offset plus the Doppler offset due to platform motion. Thus, the phase shift may be described according to equation (14) below:

$$\theta(t) = 2kx(t) + \theta_s(t) = \frac{4\pi x(t)}{\lambda} + \theta_s(t) \quad (14)$$

where x(t) is the line-of-sight distance between the heterodyne ladar and tissue surface 32, $\theta_s(t)$ is the random phase of the speckle lobe, and λ is the optical wavelength of the laser vibrometer. x(t) may change due to body vibrations and movement, laser platform vibration, and pointing jitter, for example.

The laser vibrometer sensing arrays 20 may be characterized by the carrier-to-noise ratio (CNR). More specifically, the received number of photoelectrons per second, $\phi_e$ (i.e., optical return from the vibrating tissue surface) over the vibrometer demodulated bandwidth may determine the received signal quality. The greater the number of photoelectrons received by the laser sensing system, for example, the lower the shot noise is, thus, resulting in a more sensitive laser vibrometer 20. In some embodiments, the CNR may be increased by increasing the power of the laser vibrometer 20 and by decreasing the laser beam 16 diameter that impinges upon the tissue surface 32.

The shot noise spectrum of the surface particle velocity, $A_{v,sh}$ as a function of frequency, f, may be proportional to the received returning photoelectrons as described by equation (15) below:

$$A_{v,sh}(f) = \frac{f\lambda}{\sqrt{\phi_e}} \quad (15)$$

As previously described, another source of noise may be from speckle, for example. Speckle is the noise that occurs due to the distribution of optical scatters on the tissue surface 32 encountered by the laser beam 16. For a diffuse surface, for example, there may be many scatterers (based on surface roughness) that reflect light back to the receiver. The speckle noise contribution to the laser vibrometer 20 can be reduced by signal time integration with respect to the same realization of scatterers. Increasing the integration time may reduce speckle noise and thus improve the sensitivity of the system 10. However, if during the allotted integration summing time, the laser beam 16 changes position on the target surface 32 due to platform motion, beam jitter, or target movement, for example, the speckle realization may change thereby creating translation or dynamic speckle and increase in the noise floor. Faster laser beam 16 translation speeds across the surface 32 of the patient 14 may also increase the speckle noise floor contribution. The speckle noise amplitude may be described according to equation (16) below:

$$A_{v,sp}(f) = \lambda \sqrt{\frac{\pi f_{exc}^2}{12}} \sqrt{\frac{2\alpha}{\alpha^2 + (2\pi f)^2}} \quad (16)$$

where $\alpha = 2\pi f_{exc}$ and $f_{exc} = v_t/d$ (i.e., laser beam translation velocity on target over the laser beam diameter) is the exchange rate of the speckle pattern.

Figure 4:
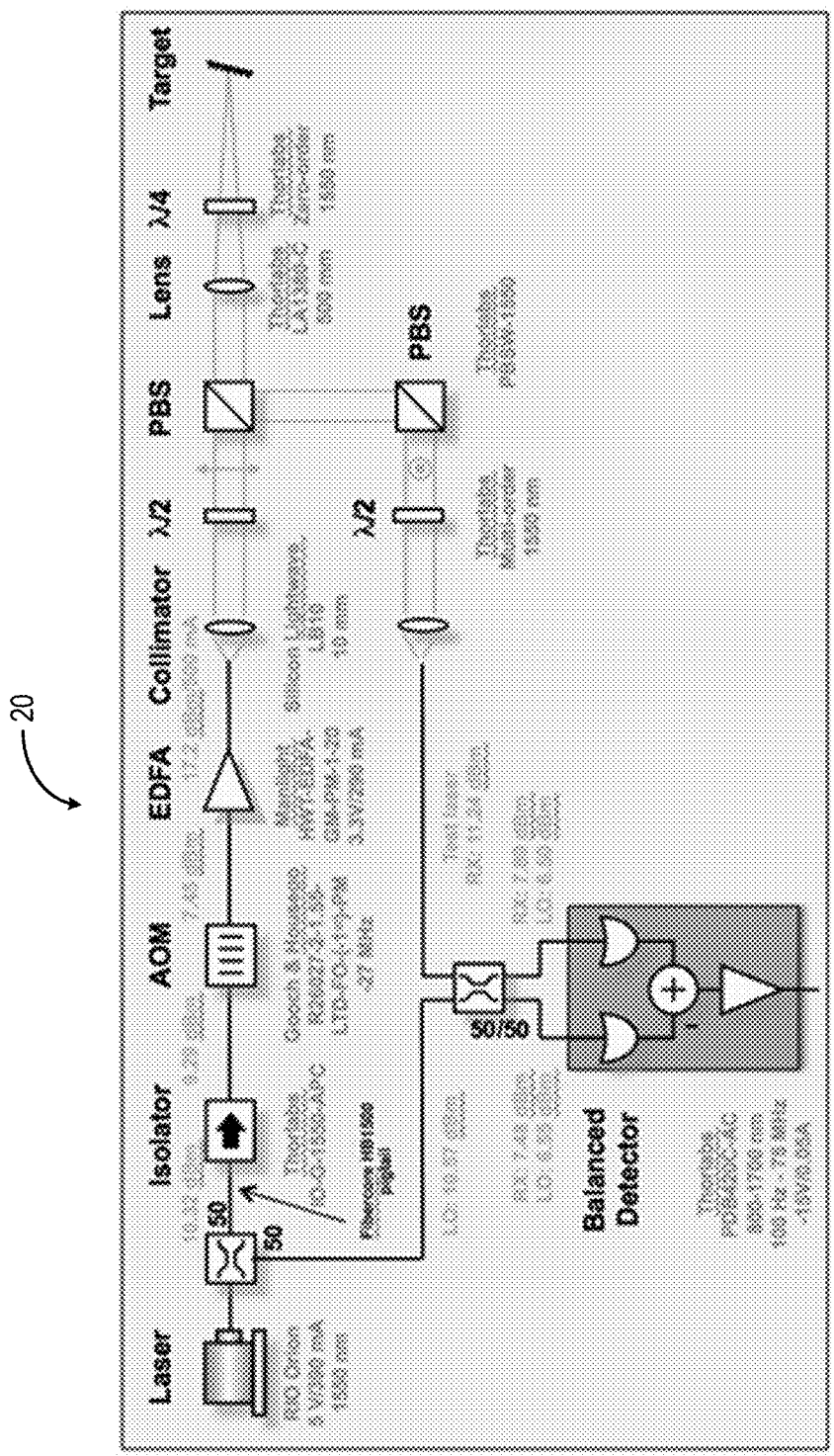
FIG. 4 is a diagram showing a laser Doppler vibrometer system configured to be implemented into the system of FIG. 1.

Performance of the laser vibrometer, such as the laser Doppler vibrometer 20 shown in FIG. 4, for ultrasonic measurements may be characterized by the shot noise contribution (e.g., at 1 MHz), for example, that is anticipated to dominate the noise floor sensitivity. However, when introducing system motion, speckle noise may become a significant factor. Even subtle motion with a small laser beam 16 diameter (on the order of millimeters) can produce significant fluctuations in the speckle realization and resultant noise floor.

In order to measure ultrasonic signals generated from the optical photoacoustic excitation source 12 utilizing the laser vibrometer 20, the system 10 may undergo a series of tests. The end result measurements from the series of tests may, in some embodiments, be conducted without coupling gels or reflexite beads for laser return enhancement or other means. The signal quality generated using the present laser vibrometer 20 may be compared to a commercial laser vibrometer, such as the laser vibrometer manufactured by Polytec, Inc., and contact ultrasonic transducers manufactured by Olympus, for example.

In a first set of transmission measurements, the direct acoustic/elastic wave transmission for through tissue samples may be measured with the laser Doppler vibrometer 20 or conventional contact ultrasonic receiving transducers. The optical source utilized may be a Continuum Q-switched 15 pulse/sec laser, for example, operating at about a 355 nm with pulse energies at the sample surface of 1-4 mJ and a spot size of 0.05 cm² yielding fluencies per pulse of 20-80 mJ/cm². The laser vibrometer beam (sensing receiver) may be aimed on an opposing side of the tissue sample, but co-located with the excitation laser beam 16. The tissue sample may be about one inch thick. Received signals measured using the laser vibrometer 20 may be recorded using the data acquisition system 24 of FIG. 1, for example. The data acquisition system 24 may include, as one example, an Agilent Technologies L4534A 20 M sample/sec digitizer. The contact transducer received signal and commercial laser vibrometer (i.e., Polytec, Inc. laser vibrometer) measurements may be recorded on a Tektronix TDS 2024B digital oscilloscope, for example.

Figure 5:
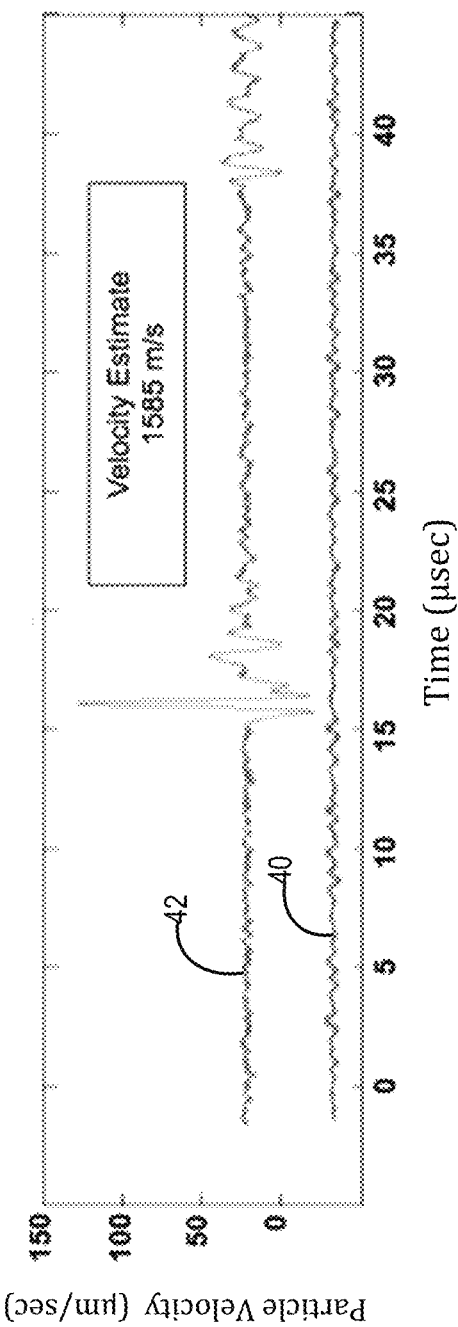
FIG. 5 is a graph showing particle velocity over time of a photoacoustically induced elastic wave through a tissue sample utilizing a conventional laser vibrometer.

In the present example, the laser Doppler vibrometer (LDV) 20 may be positioned about five feet from the tissue sample. The laser source 12, such as a Q-switched laser, is placed about one foot from the tissue sample, to initiate ultrasonic waves into the tissue sample via photoacoustic mechanisms. This configuration allows for a direct elastic wave transmission through the tissue sample. Referring to FIG. 5, the LDV measurement of direct elastic wave transmission through the tissue sample is shown using the LDV sensor. A first curve 40 shows the LDV measured response of the photoacoustically induced elastic wave when the Q-switched laser pulse is blocked with a metal plate between the excitation source and the tissue sample. A second curve 42 shows the response due to elastic wave transmission when the source beam is unimpeded. Thus, reflexite glass beads (~1 µm diameter) were necessary to achieve a reasonable SNR to detect the return signal from the surface of the tissue sample. Without the reflexite glass beads, the signal was unobservable.

However, using the present laser vibrometer 20, measurement of the direct transmission is achievable without reflexite dust. The laser vibrometer 20 achieved a better SNR due to a higher optical power of about 45 mW with a 1550 nm wavelength compared to the commercially available Polytec vibrometer power of 2 mW and 633 nm wavelength. With reference to equation (15) above, the laser vibrometer 20 may achieve a shot noise floor reduction by a factor of two better than the Polytec laser vibrometer for equal spot sizes primarily due to higher power ($\lambda/\sqrt{power}$). In addition, signal processing gains in the laser vibrometer 20 may display improved performance over the Polytec vibrometer.

Figure 6:
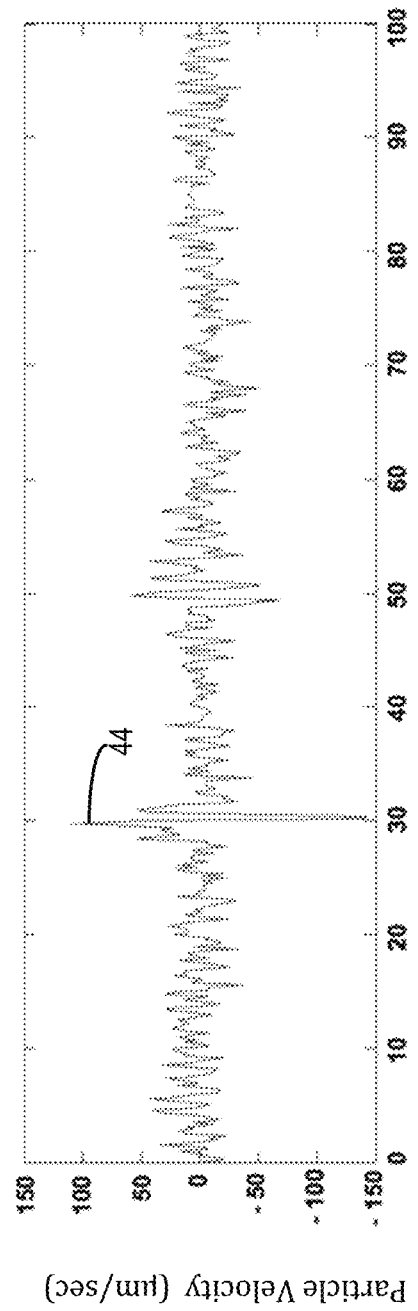
FIG. 6 is a graph showing particle velocity over time of a photoacoustically induced elastic wave through a tissue sample utilizing the system of FIG. 1.

Turning now to FIG. 6, the signal return measurement using the laser vibrometer 20 without sample surface treatment is shown. More specifically, a first curve 44 shows the response from the LDV sensor measurement of direct elastic wave transmission through the tissue sample generated by optical frequency short pulse using Q-switched laser. In this measurement example, there are no reflexite beads or any substances used to treat the sample surface to reduce the LDV noise floor response. The direct wave transmission may be observed at about 30 microseconds, and the first reflection from the back of the tissue sample may be observed at about 50 microseconds.

Figure 7:
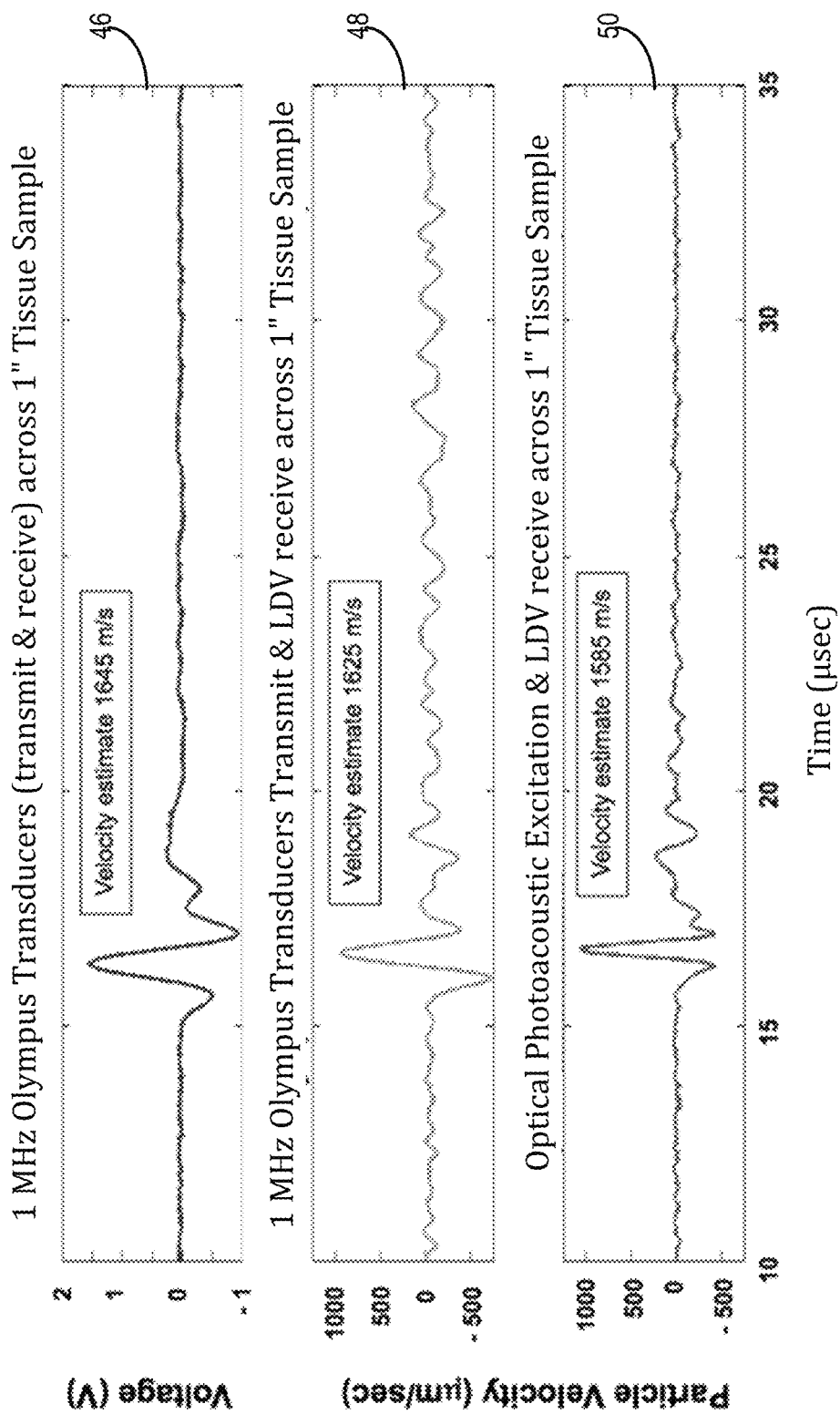
FIG. 7 is a series of graphs comparing elastic wave transmission through a tissue sample utilizing various excitation and sensor sources.

In one non-limiting example, the signal-to-noise-ratio (SNR) for combinations of contact transducers and optical devices for the direct transmission measurement configuration may be compared. As shown in FIG. 7, comparison of contact piezoelectric transducer and optical ultrasonic measurements are shown. The transmit pulse may be initiated at t=0. A first graph 46 shows the transducer transmit and receive system having direct elastic wave transmission through a one inch tissue sample in contact with and measured by a 1 MHz longitudinal transducer, for example. The contact ultrasonic source may be a 1 MHz longitudinal transducer. A second graph 48 shows the transducer transmit and LDV receive system having direct elastic wave transmission through a one inch tissue sample measured by the LDV beam pointed at the tissue sample. The ultrasonic source may be a 1 MHz longitudinal contact transducer. Lastly, a third graph 50 shows the optical transmit and LDV receive system utilizing total noncontact standoff optical ultrasound. Direct elastic wave transmission, as shown in the third graph 50 may be generated by a 355 nm Q-switched laser pulse and measured by the LDV beam pointed at an opposite side of the tissue sample, for example.

The SNR may be computed for each configuration as shown in the table of FIG. 8. The SNR may defined by equation (17) below:

$$SNR = 10 \log_{10}\left(\frac{Ps^2 - Mn^2}{Vn}\right) \quad (17)$$

where Ps is the peak signal amplitude, Mn is the mean noise, and Vn is the variance of the noise. With continued reference to FIG. 8, SNR comparisons for contact and optical ultrasonic measurement approaches indicate that the contact transducer system provides a SNR and signal quality that are better than those of optical devices without any sample treatment. The SNR is comparable for the total contact transducer arrangement compared to total optical arrangement using the Polytec with reflexite bead sample treatment (to reduce its noise floor).

However, the use of gel and axial force to hold the transducers enables coupling and has may affect the SNR. In addition, holding contact transducers in place deforms the tissue sample, such that the mechanical and transmission properties of the tissue sample are modified compared to the natural state. The observed transmission velocity, as shown in FIG. 7, is 1645 m/s and may be over estimated compared to muscle longitudinal velocities reported in the literature of 1580 m/s. The total optical measurement velocity estimate is about 1585 m/s for the optical transmit and LDV receive system, shown in FIG. 7. Thus, in the case of the total optical measurement using the laser vibrometer 20 without surface treatment to reduce the vibrometer noise floor, the SNR is the lowest, as shown in FIG. 8, and may be influenced by the reduced confining pressure on the tissue sample.

Figure 9:
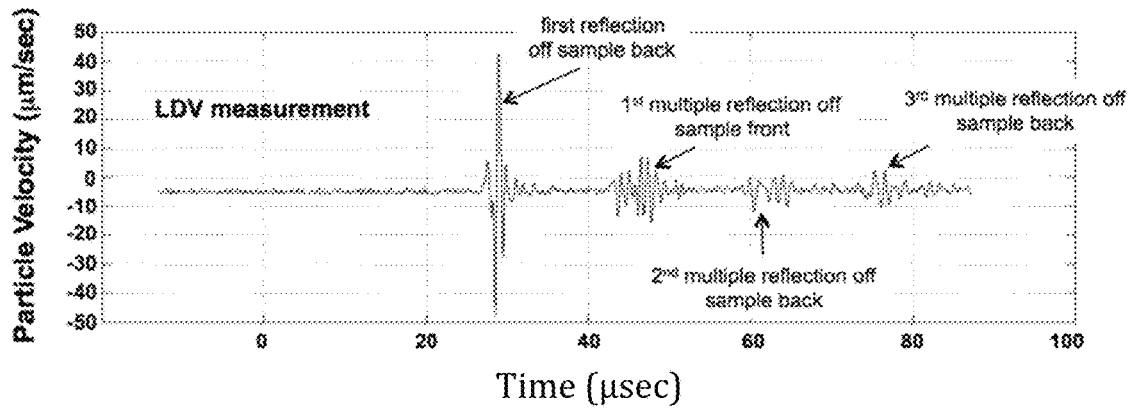
FIG. 9 is a graph showing particle velocity over time of reflected elastic wave transmission through a tissue sample for a total optical arrangement.

In another non-limiting example, a second series of measurements may be acquired by the optical excitation source 12 and laser vibrometer sensors 20. The total optical measurement configuration may be examined to analyze the reflection signal quality and probing depth of ultrasonic wave propagation. In these tests, the optical transmitter and optical sensing vibrometer may be located on the same side of the tissue sample, for example, which may be more common for use in ultrasonic imaging and probing. In one embodiment, the direct transmission configuration may be used for tomographic ultrasound imaging applications. Turning to FIG. 9, the LDV measurement of reflected elastic wave transmission through the tissue sample for the total optical arrangement where the transmitter and receiver are on the same side of the tissue sample is shown.

With continued reference to FIG. 9, the LDV and Q-switched laser are on the same side of the tissue sample. The excitation source and sensor beam spots may be approximately 0.5 inch apart on the tissue sample, and the elastic wave may be measured using the LDV sensor. The first reflected arrival from the back of the sample (i.e., tissue/air interface) shows the largest amplitude signal in FIG. 9. Subsequent multiple reflections may be observed with increasing time. The third multiple still shows a significant SNR which has experienced a travel path of four inches back and forth in the tissue sample.

Figure 10:
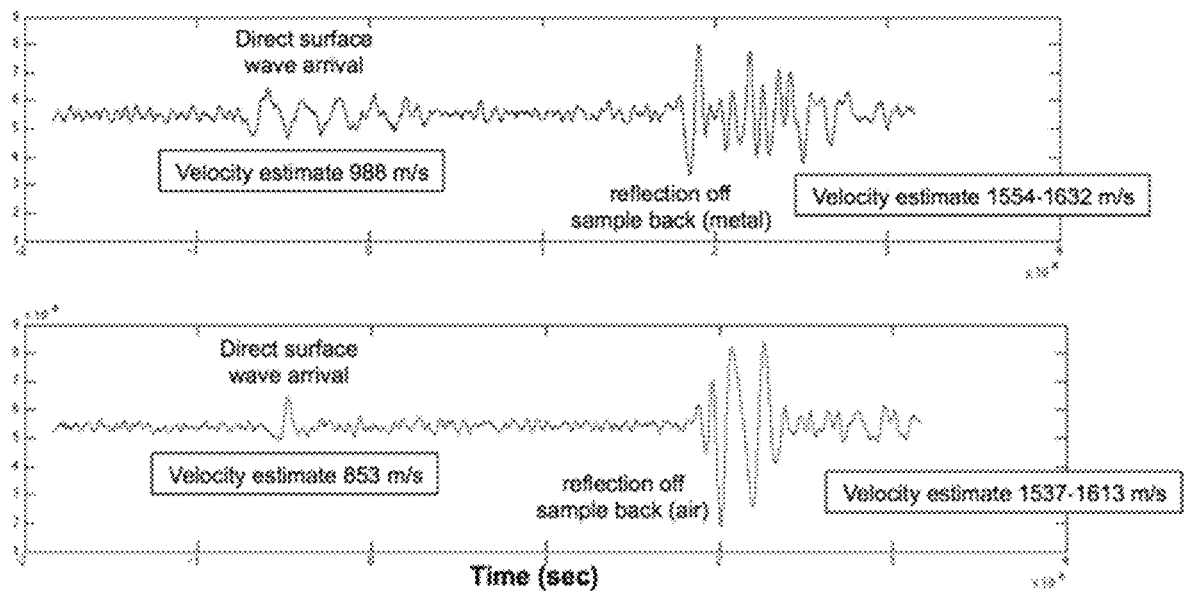
FIG. 10 is a pair of graphs showing reflected elastic wave transmission through a tissue sample utilizing a LDV measurement.

Referring now to FIG. 10, the contrast in reflection signal structure and quality for a one inch thick tissue sample is shown. In this arrangement, the Q-switched laser and LDV measure the signal from the same side of the tissue sample. The measured reflected elastic wave signal off a metal plate backing the tissue sample is shown in the top graph of FIG. 10. The metal plate is coupled to the tissue sample using a thin layer of Dow vacuum grease, for example. The signal for a tissue sample without metal backing is shown for comparison in the bottom graph of FIG. 10. The reflected signal may be attributed to the large impedance between the tissue and open air on the sample back. In both graphs of FIG. 10, the reflected signal character are noticeably different indicating that a finite plate backing the tissue sample may be imaged and mapped for different optical transmitter and sensing positions on the tissue sample face.

Figure 11:
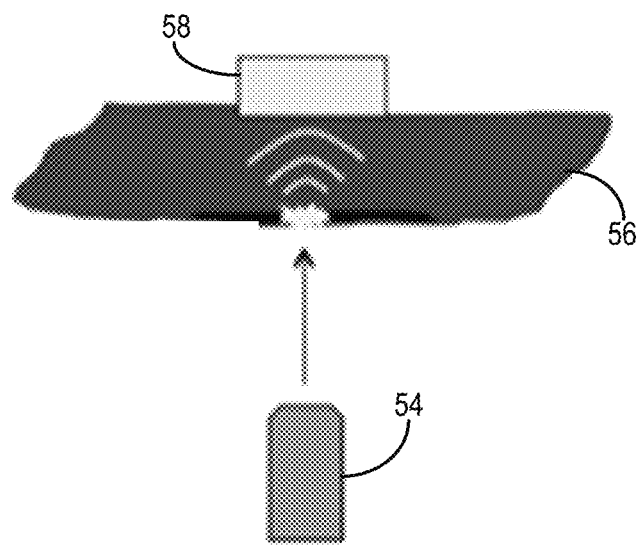
FIG. 11 is a diagram showing an example laser diode apparatus for transmitting single frequency acoustic tones utilizing an optical modulation onto a continuous wave optical carrier.

Referring now to FIG. 11, in another non-limiting example, a laser diode 54 may be used to stimulate acoustic and elastic waves in biological tissue 56 in place of the previously described Q-switched laser. The laser diodes 54 for photoacoustic excitation may include, for example, an opto-acoustic excitation source for a single channel and a line array 58. The excitation system shown in FIG. 11 may be capable of transmitting single frequency acoustic tones by employing a optical modulation onto a continuous wave optical carrier. A pulse compression technique may then be used to synthesize the acoustic-elastic wave short pulse from the received tones at the observation sensing position. A forcing function may be calculated at the source location using super position of each frequency tone over a 35 frequency chirp from about 222 kHz to about 909 kHz. Each acoustic-elastic wave tone may be measured on the opposite side of the tissue 56. Next, the measured tones may be processed using a narrow band filter, for example. Additionally or alternatively, each tone may then be summed in time to construct the short pulse.

Figure 12:
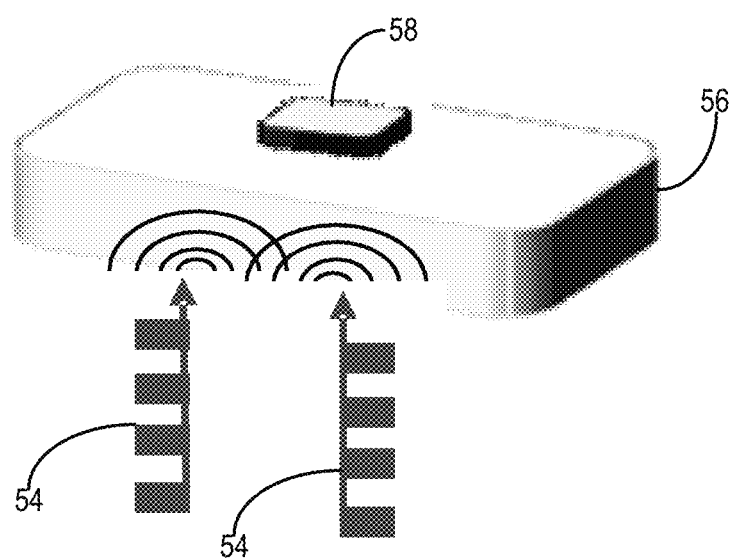
FIG. 12 is a diagram showing another example laser diode apparatus configured to transmit optically modulated carriers at continuous wave frequencies.
Figure 13:
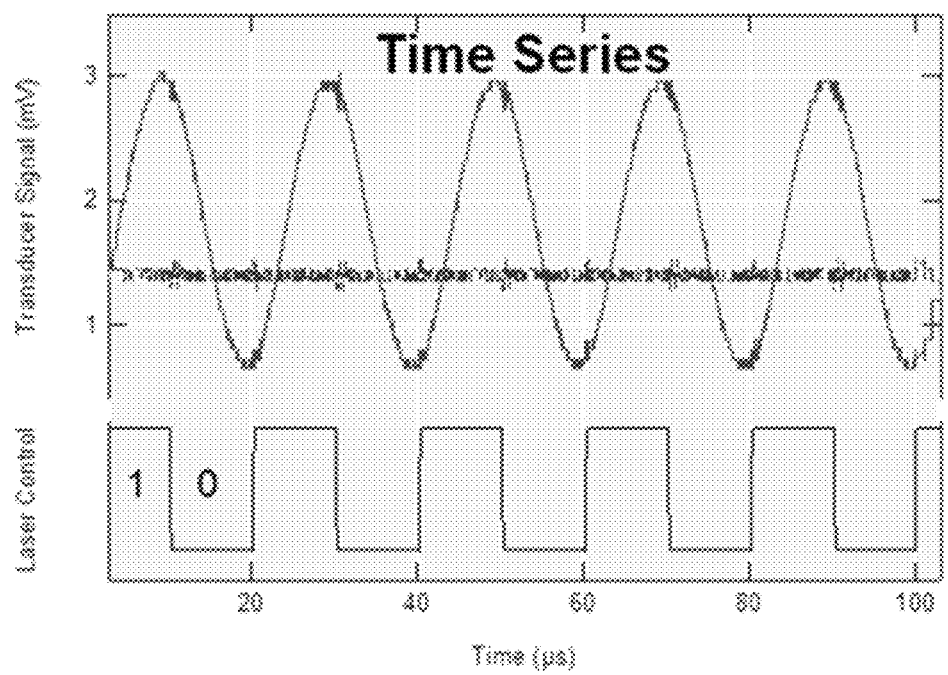
FIG. 13 is a time series graph showing a 50 kHz acoustic tone generated optically by modulating an optical carrier at a pulse repetition frequency of 50 kHz.
Figure 14:
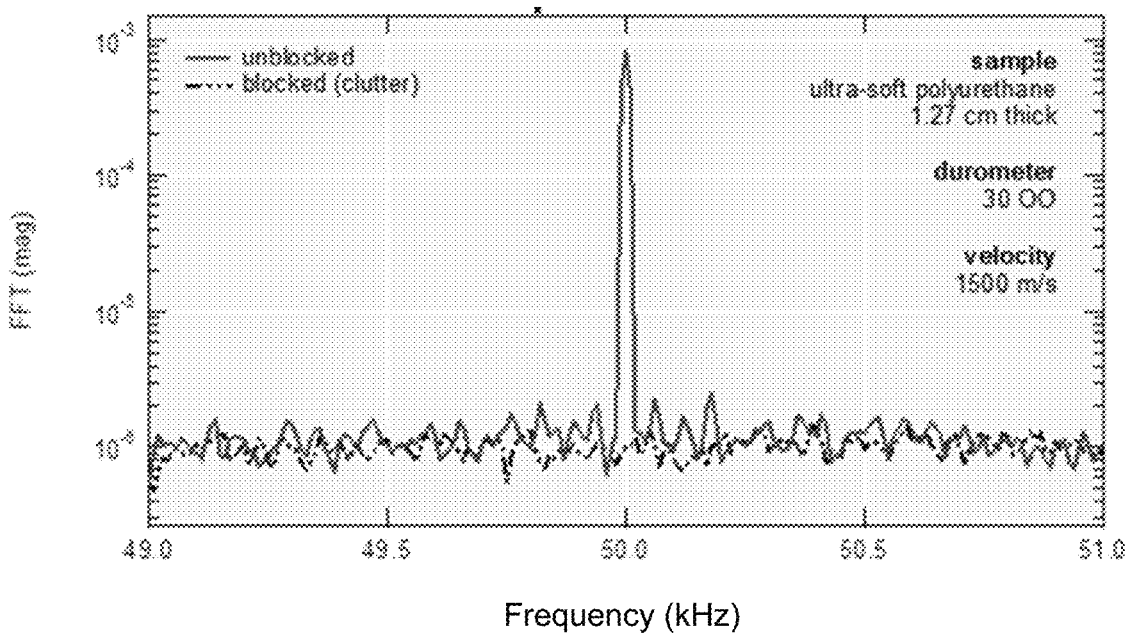
FIG. 14 a spectrum graph showing a 50 kHz acoustic tone generated optically by modulating an optical carrier at a pulse repetition frequency of 50 kHz.
Figure 15:
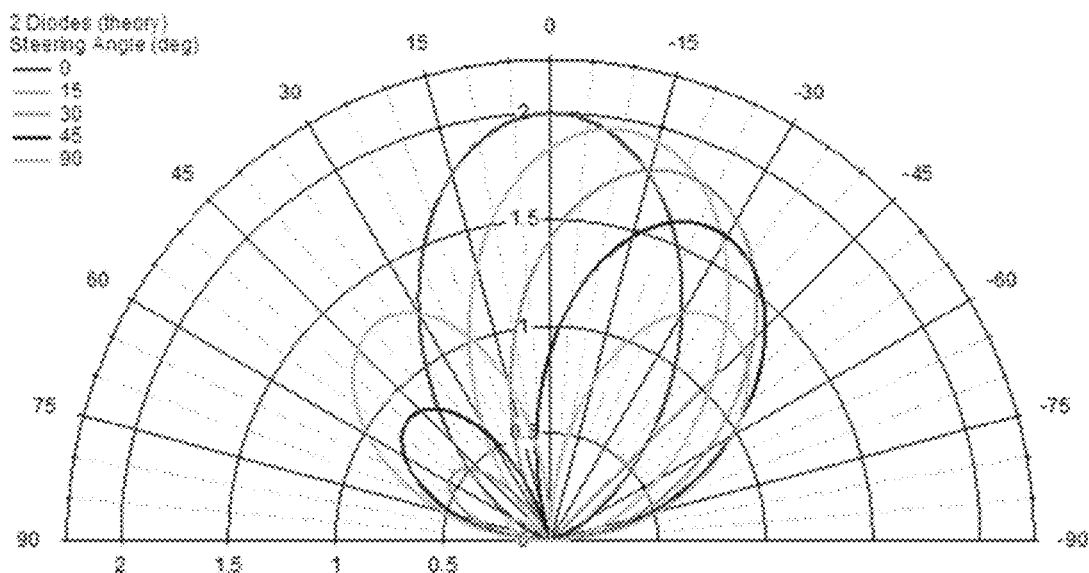
FIG. 15 is graph showing modeled acoustic beam radiation patterns.
Figure 16:
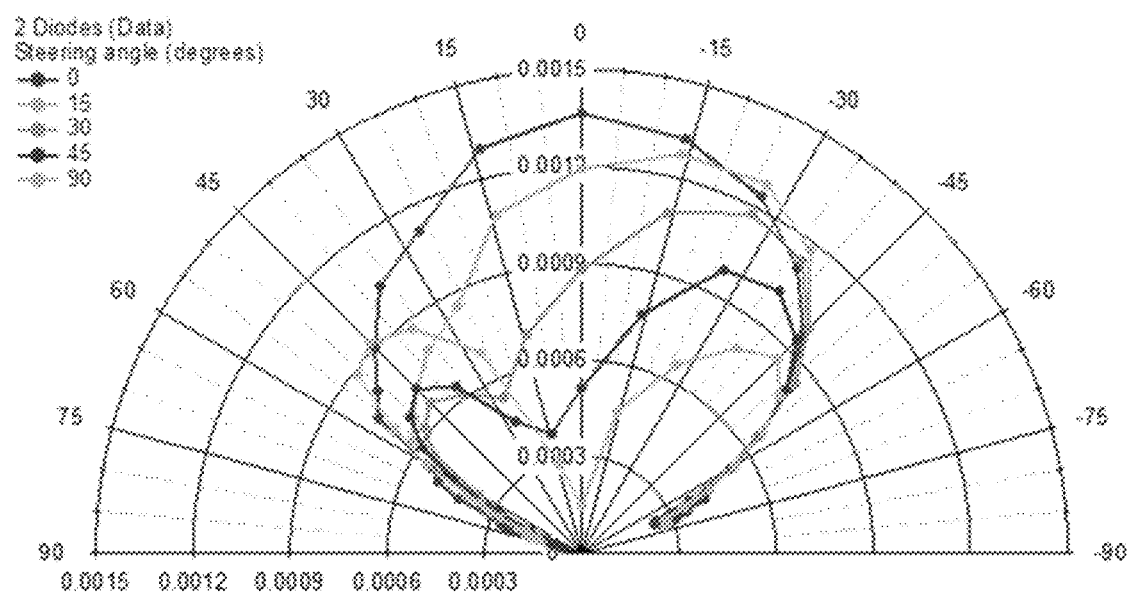
FIG. 16 is a graph showing measured beam radiation patterns corresponding to the modeled acoustic beam radiation patterns of FIG. 15.

Additionally, or alternatively, as shown in FIG. 12, two laser diode 54 elements may be used to transmit optically modulated carriers at continuous wave frequencies. The optical carrier 58, such as a piezotronics contact ultrasonic transducer, may generate the photo-acoustic response and elastic wave propagation into the biological tissue 56. The two laser diodes 54 may cause an interference pattern that can produce a steerable elastic wave, as shown in FIGS. 13 and 14. For example, as shown in FIGS. 13 and 14, a 50 kHz elastic wave frequency may be generated at the tissue sample surface due to absorption of an optical pulse at a pulse repetition frequency of about 50 kHz. As a result, the beam radiation power is generated, as shown in FIGS. 15 and 16, in response to excitation of two adjacent laser diodes 54. More specifically, FIG. 15 shows the modeled/predicted beam pattern, while FIG. 16 shows the measured pattern using a Piezotronics contact ultrasonic transducer, for example.

Figure 17:
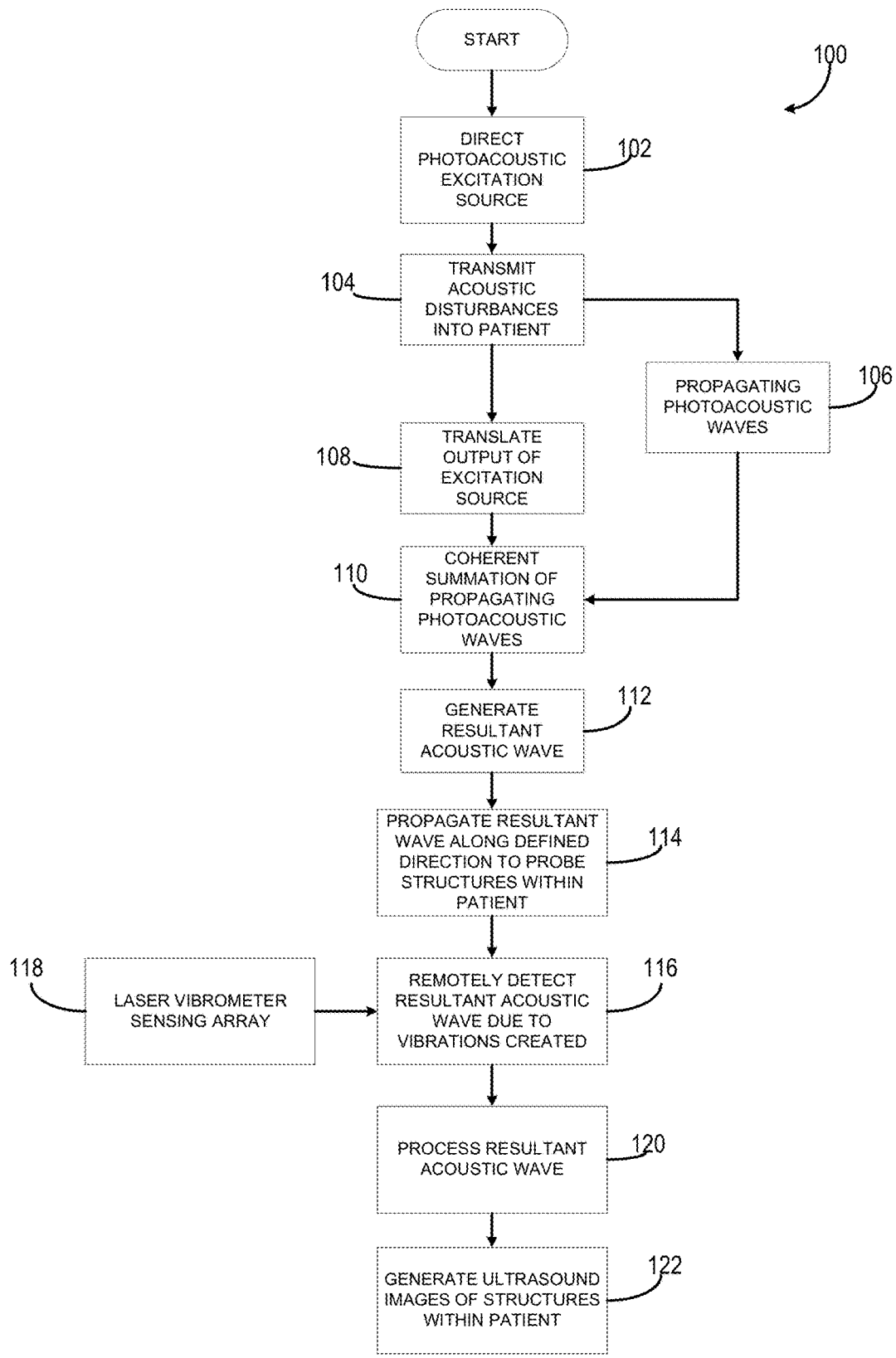
FIG. 17 is a flow chart setting forth the steps of processes for generating ultrasound images in accordance with the present invention.

Referring now to FIG. 17, a flow chart setting forth exemplary steps 100 for generating ultrasound images of structures within the patient is provided. To start the process, a photoacoustic excitation source, such as the laser source 12 shown in FIG. 3A or 3B, is directed into a scanning mirror at process block 102. The source of acoustic energy (i.e., the photoacoustic excitation source) may be, in contrast to the omni-directional acoustic energy used in conventional ultrasound imagers, a source that provides additional positional information not available via conventional ultrasound techniques. Specifically, the photoacoustic excitation source may determine not only the range to the scattering object but also its direction. It also offers the advantage over current photoacoustic techniques of a greatly enhanced signal strength.

As the laser source, for example the CW laser source, is directed into the scanning mirror, the beam is directed towards the patient, thereby transmitting acoustic disturbances into the patient at process block 104. The acoustic disturbances result in propagating photoacoustic waves across the patient at process block 106. At process block 108, output generated by the photoacoustic excitation source is translated along the patient, for example, at the speed of sound, in a defined direction to cause a coherent summation of the propagating photoacoustic waves at process block 110. The coherent summation of the propagating photoacoustic waves at process block 110 results in generation of a directional resultant wave at process block 112.

Figure 21:
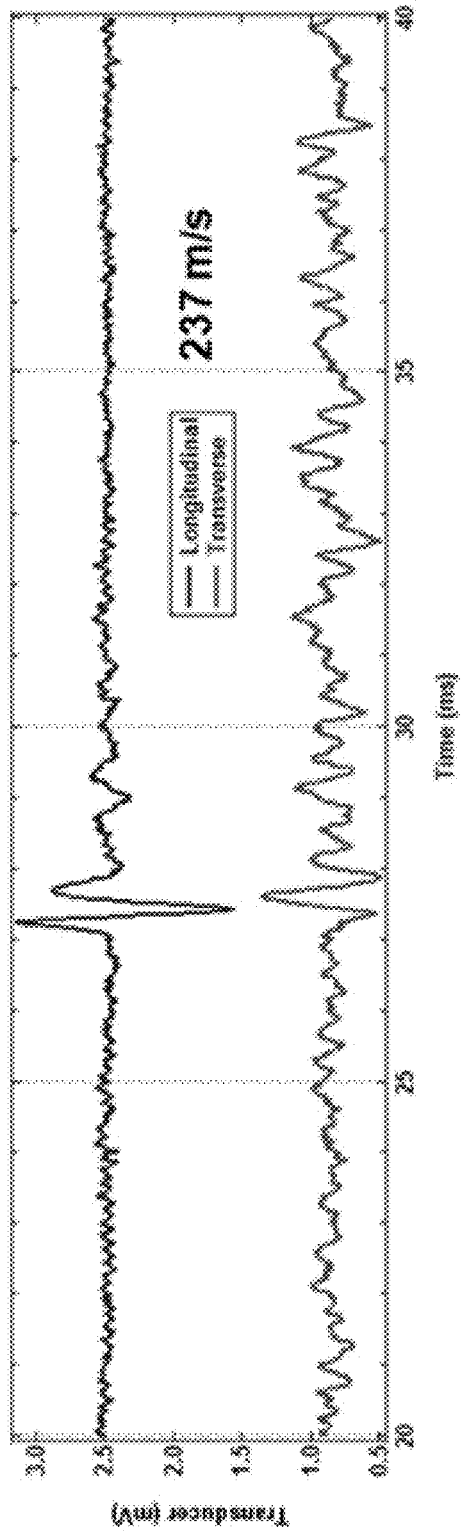
FIG. 21 is a graph showing photoacoustic signals maximized at a predetermined beam sweep speed across the skin surface sample.
Figure 22:
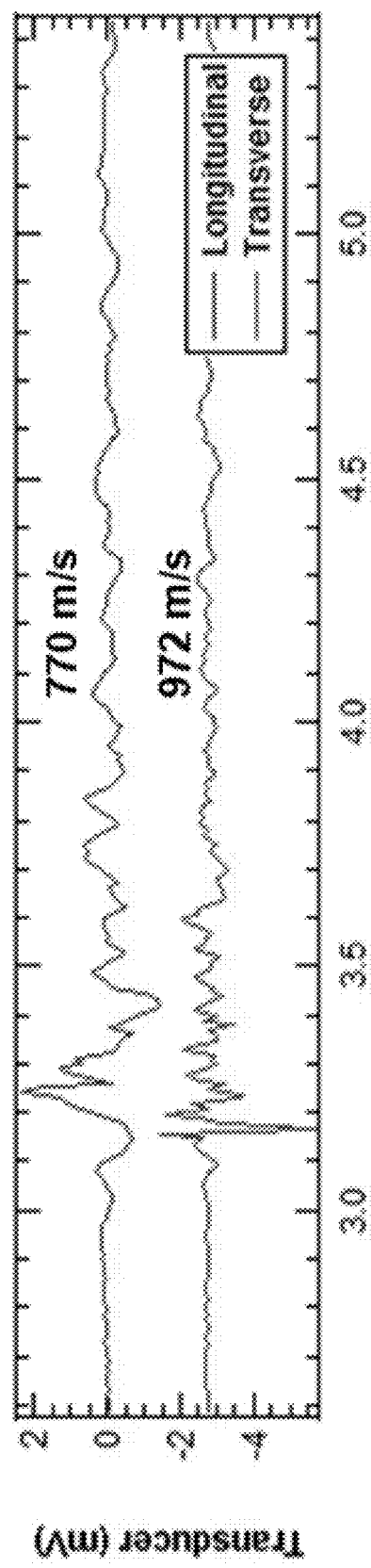
FIG. 22 is a graph showing photoacoustic signals generated at a predetermined beam sweep speeds through a bone sample.

As one example, as shown in FIG. 18, coherent summation of the propagating photoacoustic waves 180 has the advantage that the wave amplitudes, rather than intensities, add, leading to a stronger overall resultant wave 182. In addition, the scattered acoustic energy may yield information about subsurface structures. As shown in the graphs of FIGS. 19 and 20, for example, the CW laser swept at various speeds from the left side of the sample to the right side of the sample successfully induces acoustic signals. As shown in FIG. 21, the photoacoustic signal is maximized at a beam sweep speed of about 237 meters/second for a skin sample. Similarly, as shown in FIG. 22, the CW laser swept at various speeds across bone, for example, also successfully induces acoustic signals. The photoacoustic signal in this example, is maximized at about 770 meters/second in the longitudinal direction, and about 872 meters per second in the transverse direction.

Returning to FIG. 17, the resultant wave may propagate along the defined direction to probe structures of the patient's body at process block 114. At process block 116, vibrations may be detected at a surface of the patient that are created by the backscatter of the resultant wave as a result of probing structures within the patient at process block 114. The vibrations may be detected using a laser vibrometer sensing array, for example, provided at block 118. The resultant wave generated at process block 112 may then be processed at process block 120. Ultrasound images of structures within the patient may then be generated at process block 122 using the vibrations detected at the surface of the patient at process block 116.

The above-described systems and methods may be used, for example, in real-time surgical imaging guidance, detection of traumatic brain injury, internal bleeding detection and imaging, bone health monitoring, organ and tissue imaging, dynamic vital sign monitoring such as breathing rates and pulse rates from standoff. Additionally, the above-described method may be used in diagnosing vascular issues (e.g., pre-varicose veins), dermal anomalies, dehydration, BMI, or hidden sub-dermal implants.

The optical image acquisition approach described herein may have a number of advantages over contact transducer measurements. First, spatial sampling can approach sub-millimeter resolution using coherent multipixel arrays. In addition, measurements can access injured body regions, surfaces, skin conditions, open wounds or regions during surgery, difficult and awkward to reach regions, while no physical pressure of the device is applied to the skin or body. Injury to operators may be reduced due to device pressure applications to patients, and there is no need or contamination from coupling gels (as in the case of contact ultrasound devices). Lastly, the optical image acquisition approach exhibits limited SNR variability due to applied hand pressure as in the case of contact transducers.

Further features and advantages will now be discussed with respect to the selection of laser wavelengths that enhance safety, and thus the applicability and usefulness, of the above exemplary systems and methods and implementations thereof. Specifically, an optimal wavelength range enabling noncontact ultrasound imagery utilizing photoacoustics to create a directed source of acoustic energy within the body in a manner that is safer for the eyes and skin will be further discussed.

As noted above, typical studies of photoacoustics have focused on wavelengths below about 1100 nm. The discussion now shifts to a study extending wavelengths to 2000 nm in determining a specific wavelength range capable of maximizing signal levels while maintaining an eye and skin safe level. This would be extremely useful in creating penetrating acoustic energy within the human body while maintaining safety margins. As further discussed below, an exemplary range capable of achieving these safety goals is 1400 to 1600 nm. Based on analyses of the data coupled with the known absorption of tissue, 1550 nm and nearby wavelengths may be chosen, for example, as preferred exemplary wavelengths for use in biomedical photoacoustics in which penetrating acoustic energy is desired.

Returning to FIGS. 1 and 2, in exemplary versions, an excitation source 12 may generate a laser beam 16 with an optical wavelength between 1400 and 1600 nm, such as 1550 nm or nearby wavelengths, to create a propagating acoustic wave within the human body. This acoustic wave may be used to probe the internal structure of the body as discussed above, with greatly enhanced signal strength.

Detection of scattered acoustic energy would also preferably be achieved in a noncontact manner. As the acoustic waves are backscattered towards the surface they induce a vibration at the surface, which can be sensed using, for example, laser vibrometer 20. Exemplary laser vibrometers 20 function as interferometers that send out an eye and skin safe beam of light and examine the phase shifts of the backscattered return. Motion at the reflecting surface induces phase shifts detectable by the vibrometer.

Exemplary configurations of a full noncontact system could contain integrated transmit and receive laser subsystems. The beams from the subsystems could potentially be collocated on the subject such that relative delays on the individual receive signals would optimize the measured signal in the appropriate direction (in a manner analogous to the receive antenna in a phased array radar). A schematic image of such a potential system 10 is illustrated in FIG. 2.

Figure 23:
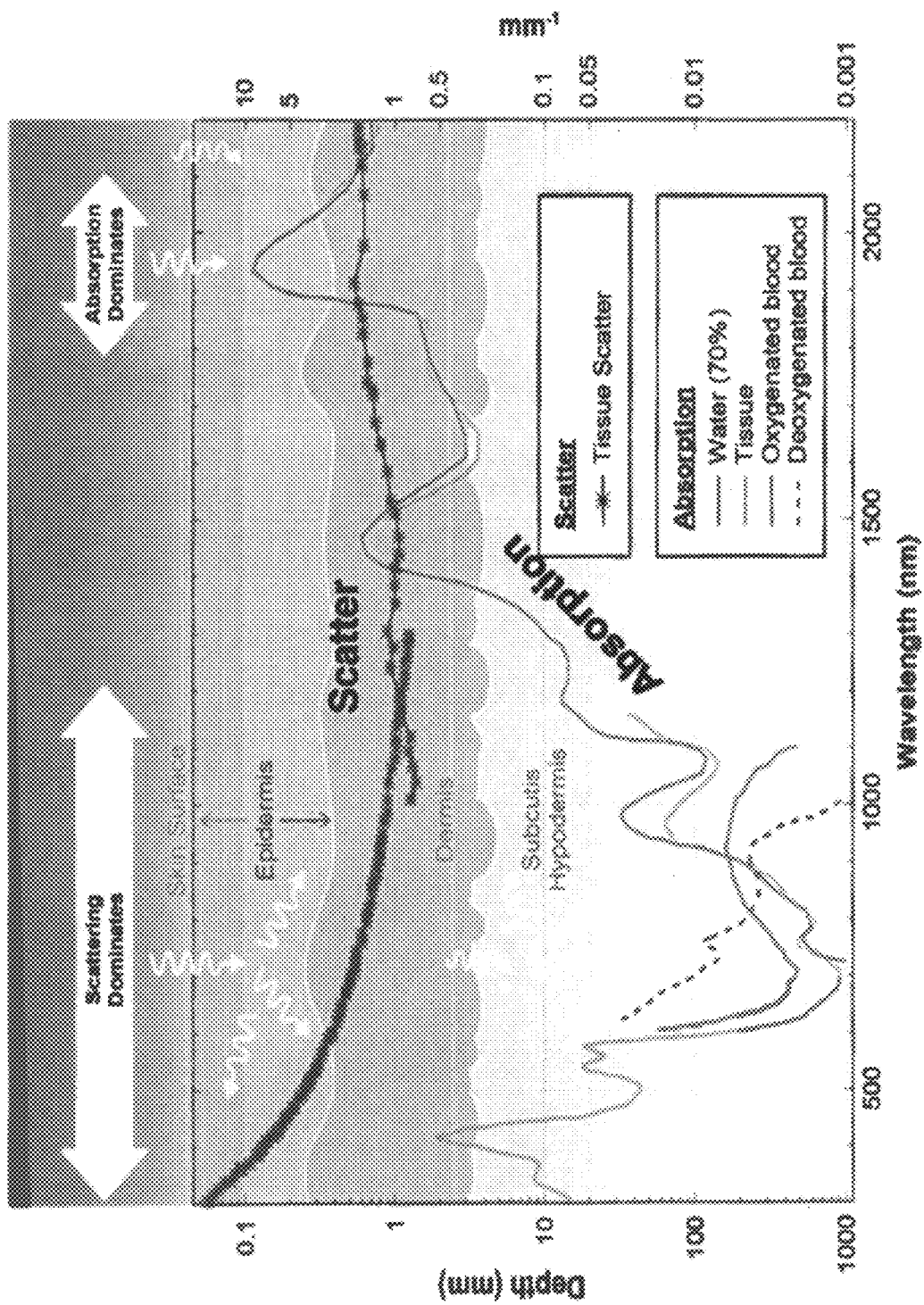
FIG. 23 illustrates optical properties of tissue and its related components, with both absorption and scattering displayed as a function of optical wavelength of a source laser.

Referring to FIG. 23, it has been observed that in the visible to the near infrared range, scattering dominates the optical response. Throughout much of this region of the spectrum, scattering is a significant factor governing the optical response of the tissue in that it generally occurs on a shorter length scale than optical absorption. The optical response of tissue is very similar to that of water in the near infrared.

Figure 24:
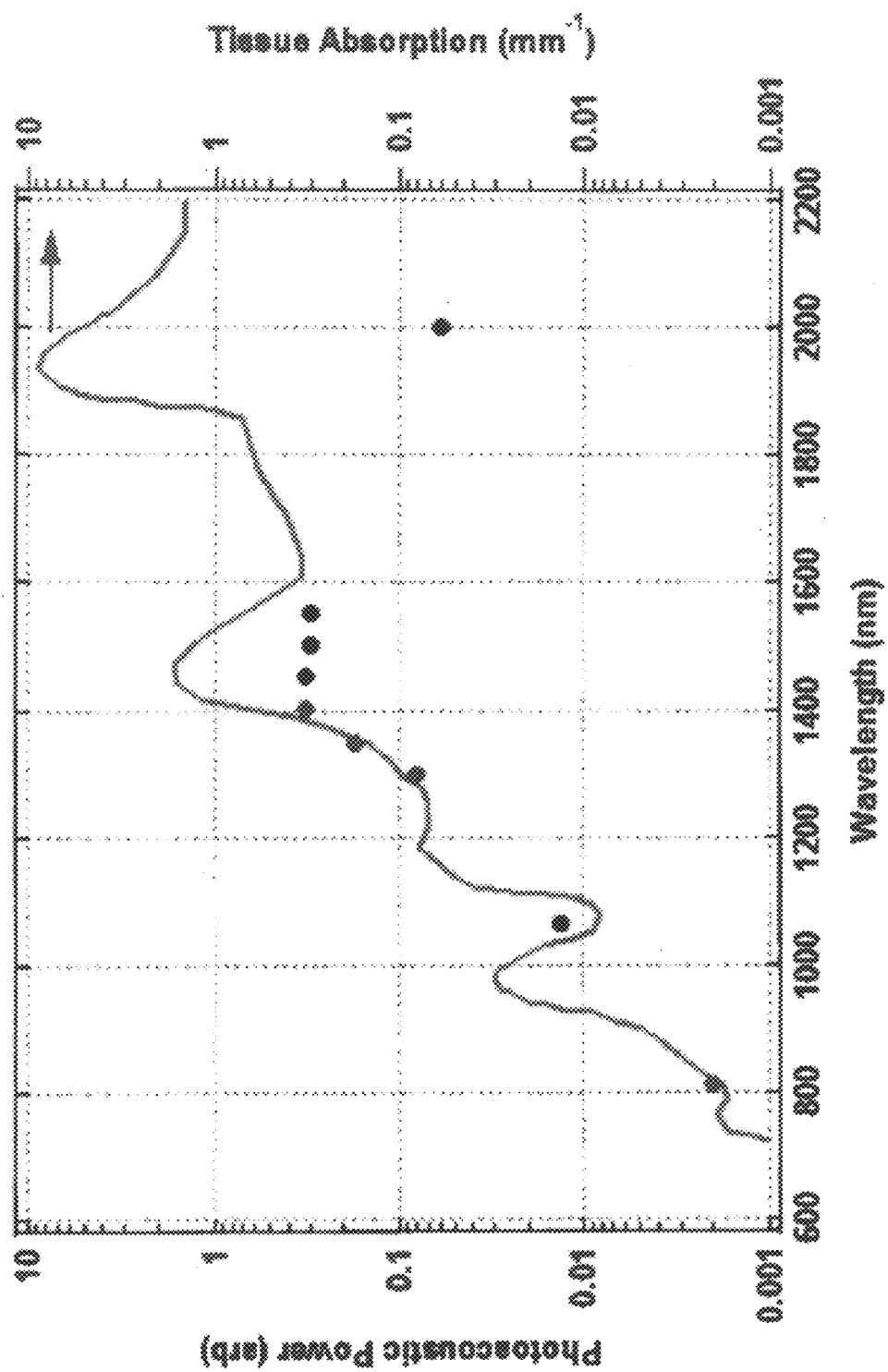
FIG. 24 illustrates that the photoacoustic energy generated by a pulsed laser at various wavelengths on the left-hand side, with tissue absorption (FIG. 23) overlaid on the right-hand side.

An interesting and very useful relationship between the optical properties of tissue and the photoacoustic energy that results can be observed. This relationship corresponds with the specifics of the optimum means of generating photoacoustic energy in the body. Using a tunable (optical parametric oscillator) Q-switched laser as source 12, the photoacoustic response in steak samples was measured as a function of optical wavelength. The laser was operated at a 30 Hz repetition rate with approximately 7 ns pulses. The laser spot size was 2 mm. The laser fluence was fixed at 21 mJ/cm$^2$ (0.8 mJ/pulse; 25 mW average power). It was found that the photoacoustic power tracks the tissue absorption in the visible region (FIG. 24). However, in the infrared region it reaches a maximum in the wavelength range spanning 1400 to 1600 nm. The power decreases as the wavelength is increased further. Based on these measurements, 1400 to 1600 nm is an optimal wavelength range to use for photoacoustic imaging of the human body.

Figure 25:
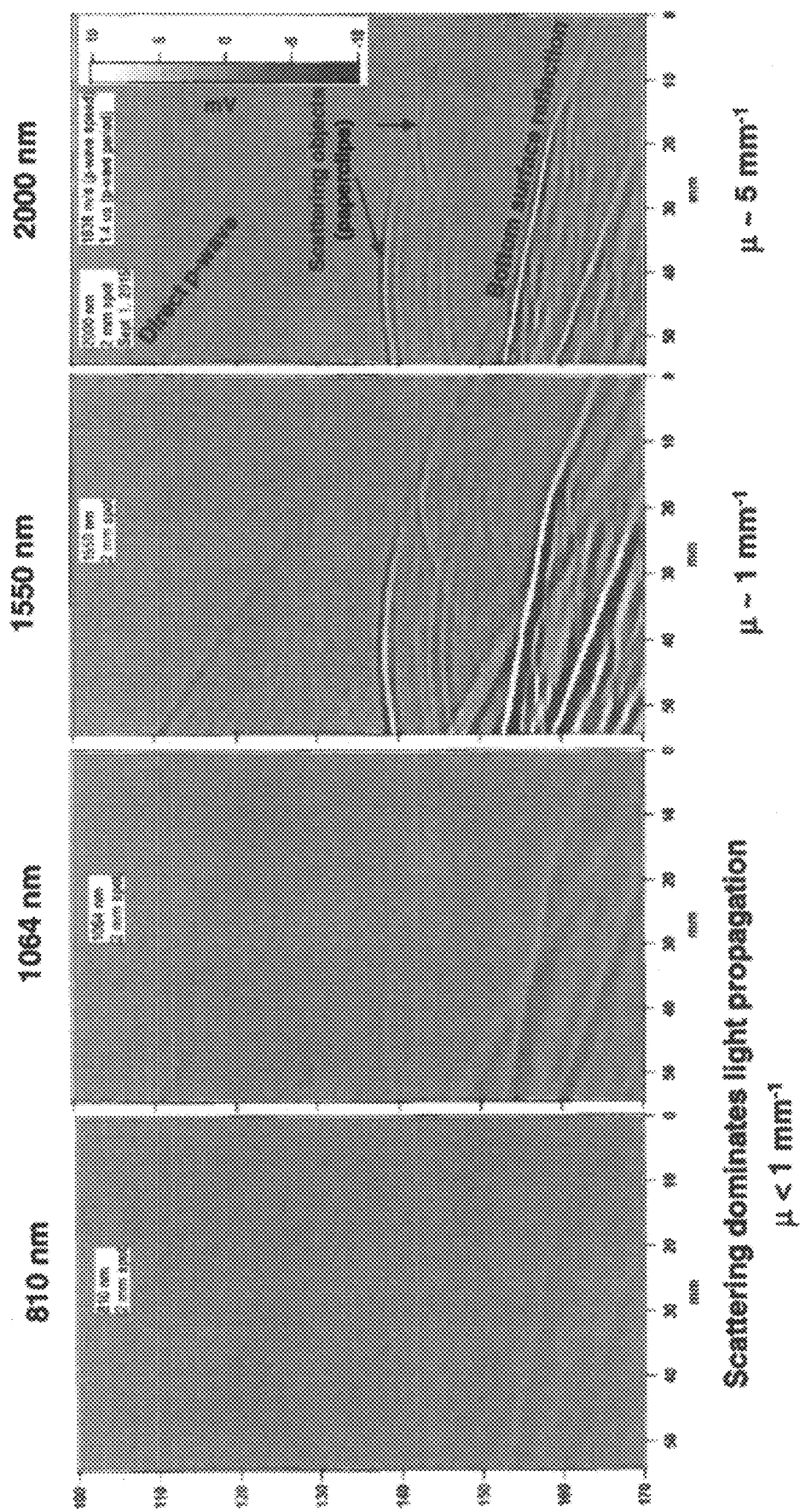
FIG. 25 provides photoacoustic images of steak with embedded objects at various wavelengths.

With this insight, sonogram images of steak samples were created with the same exemplary laser system (i.e., 2 mm spot, 30 pulses per second, 0.8 mJ per pulse, 7 ns per pulse, with optical power of 25 mW and fluence of 21 mJ/cm2), and several characteristic images are shown in FIG. 25. The laser energy was constant with each laser wavelength. The most energy (and best contrast imagery) was observed at 1550 nm, consistent with the above results. That is, among the wavelengths shown in these images, 1550 nm light created the largest photoacoustic response. This is the first demonstration of photoacoustic imagery using an optimized optical wavelength system. It is noted that while a Q-switched laser was used to generate these images, other laser types (such as fiber laser, diode laser, etc.) could be used, as long as light in the desired wavelength range can be produced.

It is noted that sonograms may be generated by using how long it takes for echoes to be received, which corresponds with positions of structures being imaged, and the strength of the echoes, which corresponds with the mechanical properties of the structures at the corresponding positions. In forming an image for display, the strength of the echoes may be correlated with, for example, the brightness or darkness of pixels at corresponding positions. Different modes of sonography may be used, such as "A-mode" (amplitude mode), which plots echoes on a screen as a function of depth.

Figure 26B:
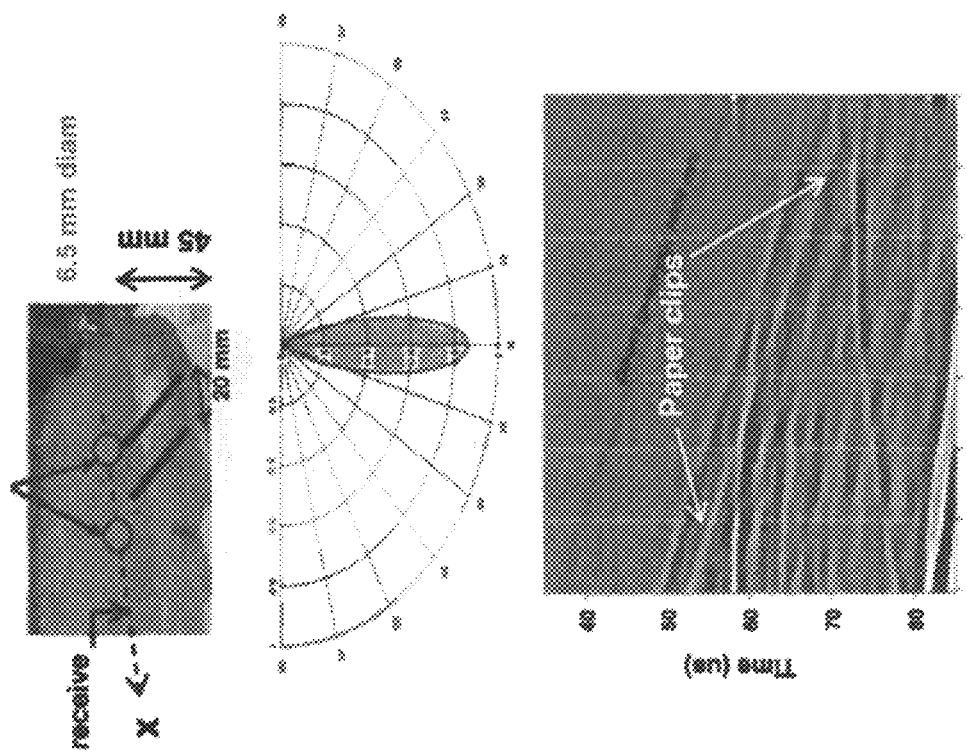
FIG. 26B illustrates the relationship between a relatively large laser spot size on acoustic directivity.
Figure 26A:
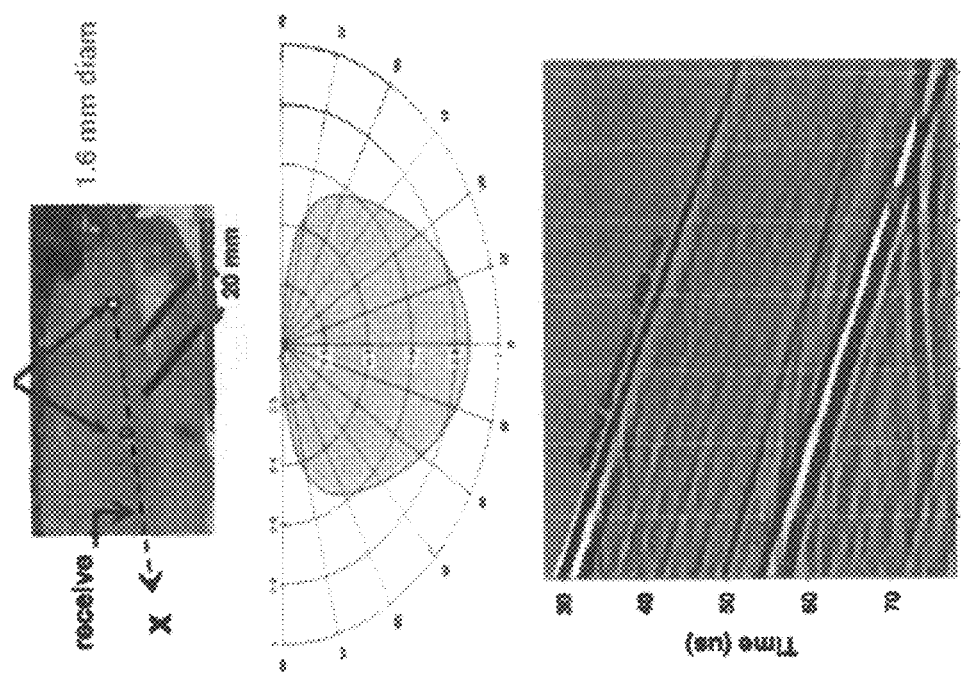
FIG. 26A illustrates the relationship between a relatively small laser spot size on acoustic directivity.

FIGS. 26A and 26B illustrate the effects of excitation laser spot size on acoustic directivity for radiated acoustic energy (1550 nm, pulse energies of 2 mJ). Here, 1 mm paper clips were inserted into the steak at depths of 20 mm and 30 mm. In FIG. 26A, the small spot laser had a diameter of 1.6 mm and a fluence of 78 mJ/cm$^2$, and the large laser spot size in FIG. 26B had a diameter of 6.5 mm with a fluence of 4.7 mJ/cm$^2$. It was observed that larger excitation laser spot size helps sharpen acoustic directivity, improve down-looking SNR, and minimize "out-of-plane" scattering while reducing optical power well within safety limits.

Figure 27:
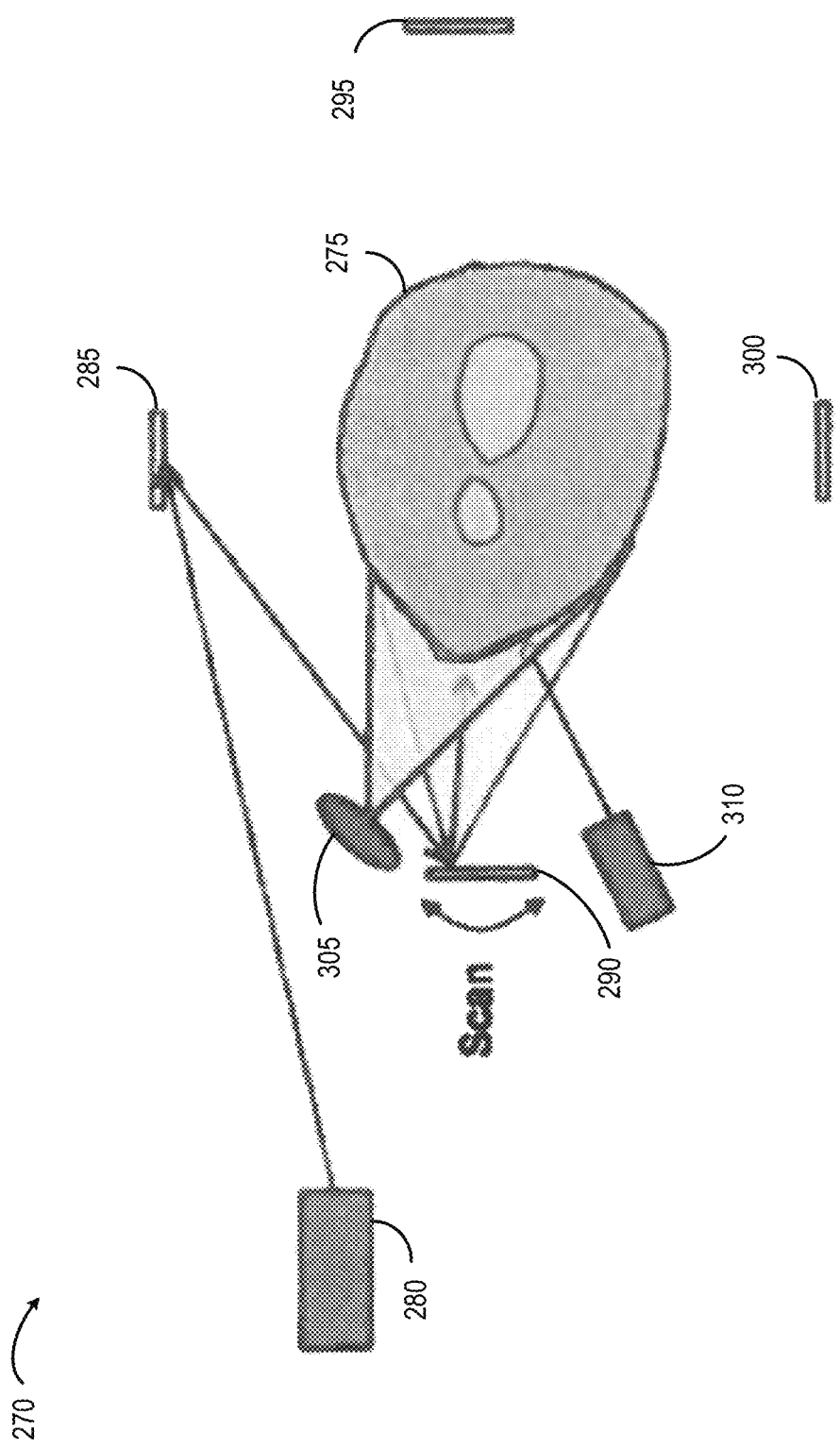
FIG. 27 depicts an exemplary configuration for a 4-mirror system for full-coverage tomography of specimens.

Referring to FIG. 27, an exemplary 4-mirror system 270 for full coverage tomography (3D imaging) of specimen 275 is provided. In system 270, an optical parametric oscillator (OPO) 280, such as a Q-switch laser, can vary excitation wavelength (e.g., from deep UV to near IR). OPO 280 can produce a laser beam directed at a first scanning mirror 285, which can reflect the beam to a second scanning mirror 290. In this configuration, system 270 also includes third and fourth mirrors 295, 300. A short-wave infrared imaging (SWIR) camera 295 (which may cover the range of wavelengths from 700 to 1700 nm, for example) is able to register laser spot locations on skin for fixed references. A laser Doppler velocimetry (LDV) sensor 300, such as a laser vibrometer and transducer, is capable of measuring optically-induced ultrasound signals.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating ultrasound images of a subject, the method comprising the steps of:
   a) directing light signals from a photoacoustic excitation source into a subject to generate acoustic energy that induces propagating photoacoustic waves, wherein the light signals have a wavelength between about 1400 and about 1600 nanometers;
   b) translating the acoustic energy relative to the subject in one or more defined directions to cause a coherent summation of the propagating photoacoustic waves and, thereby, generate at least one resultant wave that propagates along the defined direction to probe structures within the subject;
   c) detecting vibrations at a surface of the subject created by scattering of the at least one resultant wave from the structures within the subject; and
   d) generating ultrasound images of the structures within the subject using the vibrations detected at the surface of the subject in step c).

2. The method of claim 1, wherein the ultrasound images are sonograms.

3. The method of claim 2, wherein the method further comprises analyzing the sonograms to generate wave features indicative of tissue properties.

4. The method of claim 1, wherein the light signals have a wavelength of about 1550 nanometers.

5. The method of claim 1, wherein the photoacoustic excitation source does not contact the subject.

6. The method of claim 1, wherein the photoacoustic excitation source comprises a laser, a directed source of radio frequency energy, or a directed source of microwave energy.

7. The method of claim 1, further comprising translating the acoustic energy at a speed of sound.

8. The method of claim 1, wherein the light signals are directed using a scanning mirror, and wherein the method further comprises translating the acoustic energy by movement of at least one of the scanning mirror and the photoacoustic excitation source.

9. The method of claim 1, wherein the method further comprises detecting vibrations at the surface of the subject using at least one of a laser vibrometer sensing array and an ultrasonic transducer receiver.

10. The method of claim 9, wherein the laser vibrometer sensing array emits a beam of light configured to be delivered to at least one of an eye and skin of the subject.

11. The method of claim 9, further comprising performing Doppler tracking using the laser vibrometer sensing array to compensate for movement of the subject.

12. The method of claim 1, further comprising generating three-dimensional (3D) images of a brain of the subject or a bone of the subject.

13. The method of claim 1, further comprising using the generated ultrasound images as real-time feedback during surgery, wherein generation of the ultrasound images does not require contact with the subject being operated on.

14. A system for generating ultrasound images of a subject, the system comprising:
   a photoacoustic excitation source configured to generate light signals that induce acoustic energy propagating as photoacoustic waves in a subject;
   a scanning mirror configured to direct light signals from the photoacoustic excitation source to multiple locations in the subject;
   a sensor configured to detect vibrations at a surface of the subject and comprising at least one of a laser vibrometer sensing array and an ultrasonic transducer receiver;
   a data acquisition system configured to acquire data associated with vibrations detected by the sensor;
   a processor, having access to the data acquisition system, configured to carry out the steps of:
   (i) using the photoacoustic excitation source to generate light signals having a wavelength between about 1400 and about 1600 nanometers to induce the acoustic energy in a subject;
   (ii) controlling a translation of the acoustic energy along the subject in a defined direction to cause a coherent summation of the propagating photoacoustic waves and, thereby, generate at least one resultant wave that propagates along the defined direction;
   (iii) measuring, using the data acquisition system and sensor, vibrations at the surface of the subject created by scattering of the at least one resultant wave from the structures within the subject; and
   (iv) generating ultrasound images of the structures within the subject using the vibrations detected at the surface of the subject in step (iii).

15. The system of claim 14, wherein the ultrasound images are sonograms, and wherein the processor further carries out the step of analyzing the sonograms to generate wave features indicative of tissue properties.

16. The system of claim 14, wherein the processor is configured to use the photoacoustic excitation source to generate light signals having a wavelength of about 1550 nanometers.

17. The system of claim 14, wherein the system is configured to generate ultrasound images without contacting the subject with the photoacoustic excitation source.

18. The system of claim 14, wherein the photoacoustic excitation source comprises a laser, a directed source of radio frequency energy, or a directed source of microwave energy.

19. The system of claim 18, wherein the laser has one of a continuous wave output and an output with a modulating frequency between about 0 kHz and about 10 MHz.

20. The system of claim 18, wherein at least one of the scanning mirror and the photoacoustic excitation source is configured to perform a movement to translate the acoustic energy.

21. The system of claim 18, wherein the processor is further configured to generate three-dimensional (3D) images of a brain of the subject or the bone of the subject.

22. The system of claim 14, wherein the laser vibrometer sensing array emits a beam of light configured to be delivered to at least one of an eye and skin of the subject.

23. The system of claim 14, wherein the laser vibrometer sensing array comprises at least one of a coherent multipixel imaging system and a digital focal plane array that is configured to measure the vibrations at the surface of the patient over a frequency band of about 1 Hz to about 40 MHz.

24. A method for generating ultrasound images of a patient, the method comprising the steps of:
   a) directing a laser source configured to produce a laser beam having a wavelength between about 1400 and about 1600 toward the patient to induce propagating photoacoustic waves;
   b) translating the laser beam relative to the patient in one or more defined directions to cause a coherent summation of the propagating photoacoustic waves and, thereby, at least one resultant wave that propagates along the defined direction to probe structures within the patient;
   c) detecting vibrations, using a laser vibrometer sensing array, at a surface of the patient created by backscatter of the at least one resultant wave from the structures within the patient; and
   d) generating ultrasound images of the structures within the patient using the vibrations detected at the surface of the patient in step c).

* * * * *

UNITED STATES PATENT AND TRADEMARK OFFICE
CERTIFICATE OF CORRECTION

PATENT NO.        : 10,602,931 B2
APPLICATION NO.   : 15/458671
DATED             : March 31, 2020
INVENTOR(S)       : Charles M. Wynn et al.

It is certified that error appears in the above-identified patent and that said Letters Patent is hereby corrected as shown below:

In the Specification

Column 7, Line 27-28, "14, or example" should be --14, for example--.

Signed and Sealed this
Fifth Day of May, 2020

Andrei Iancu
*Director of the United States Patent and Trademark Office*